(12) United States Patent
Kemp et al.

(10) Patent No.: US 12,343,514 B2
(45) Date of Patent: Jul. 1, 2025

(54) DRUG DELIVERY DEVICE WITH FEEDBACK MECHANISM

(71) Applicant: SANOFI-AVENTIS DEUTSCHLAND GMBH, Frankfurt am Main (DE)

(72) Inventors: Thomas Mark Kemp, Ashwell Herford (GB); Hugo Revellat, Royston (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 19/028,358

(22) Filed: Jan. 17, 2025

(65) Prior Publication Data

US 2025/0161575 A1 May 22, 2025

Related U.S. Application Data

(63) Continuation of application No. 18/968,712, filed on Dec. 4, 2024, which is a continuation of application
(Continued)

(30) Foreign Application Priority Data

Jun. 3, 2015 (EP) ..................................... 15170590

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/3245* (2013.01);
(Continued)

(58) Field of Classification Search
CPC ........ A61M 5/3157; A61M 2005/2013; A61M 5/2033; A61M 5/3257; A61M 5/3258; A61M 5/326; A61M 2005/208
See application file for complete search history.

(56) References Cited

U.S. PATENT DOCUMENTS 4,629,454 A 12/1986 Grier
4,693,711 A 9/1987 Bremer et al.
(Continued)

FOREIGN PATENT DOCUMENTS

CN 200987443 Y 12/2007
CN 101107032 A 1/2008
(Continued)

OTHER PUBLICATIONS

U.S. Appl. No. 16/759,488, filed Apr. 27, 2020, Revellat et al.
(Continued)

*Primary Examiner* — Nilay J Shah
(74) *Attorney, Agent, or Firm* — Fish & Richardson P.C.

(57) ABSTRACT

A drug delivery device includes a case adapted to hold a medicament container, a plunger disposed within the case and slidable from a proximal position into a distal position for delivering a medicament from the medicament container, at least one feedback mechanism that is in operative connection with the plunger. The feedback mechanism comprises a collar, a control spring biasing the collar in a distal direction, a needle shroud, operatively axially abutting the collar in a first coupled state and prevented from axially decoupling the collar by the plunger in its proximal position The plunger, when approaching the distal position during movement from the proximal position towards the distal position, is adapted to allow axial decoupling of the needle shroud from the collar, allowing for a limited axial movement of the collar relative to the needle shroud until the collar axially abuts the needle shroud in a second coupled state.

30 Claims, 20 Drawing Sheets

Related U.S. Application Data

No. 17/172,602, filed on Feb. 10, 2021, now Pat. No. 12,186,540, which is a continuation of application No. 15/578,668, filed as application No. PCT/EP2016/062455 on Jun. 2, 2016, now Pat. No. 10,940,270.

(52) U.S. Cl.
CPC .............. *A61M 2005/208* (2013.01); *A61M 2005/3247* (2013.01); *A61M 2005/3267* (2013.01); *A61M 2205/581* (2013.01); *A61M 2205/582* (2013.01)

(56) References Cited

U.S. PATENT DOCUMENTS

| | | | |
|---|---|---|---|
| 4,810,249 A | 3/1989 | Haber et al. |
| 5,114,406 A | 5/1992 | Gabriel et al. |
| 5,116,313 A | 5/1992 | McGregor |
| 5,127,906 A | 7/1992 | Landry et al. |
| 5,271,527 A | 12/1993 | Haber et al. |
| 5,391,157 A | 2/1995 | Harris et al. |
| 7,597,685 B2 | 10/2009 | Olson |
| 7,611,495 B1 | 11/2009 | Gianturco |
| 7,918,824 B2 | 4/2011 | Bishop et al. |
| 8,409,138 B2 | 4/2013 | James et al. |
| 8,734,394 B2 | 5/2014 | Adams et al. |
| 8,979,807 B2 | 3/2015 | Grunhut et al. |
| 9,044,553 B2 | 6/2015 | James et al. |
| 9,168,339 B2 | 10/2015 | Cowe |
| 9,199,038 B2 | 12/2015 | Daniel |
| 9,216,251 B2 | 12/2015 | Daniel |
| 9,216,256 B2 | 12/2015 | Olson et al. |
| 9,233,213 B2 | 1/2016 | Olson et al. |
| 9,402,957 B2 | 8/2016 | Adams et al. |
| 9,408,976 B2 | 8/2016 | Olson et al. |
| 9,744,306 B2 | 8/2017 | Cowe |
| 9,764,096 B2 | 9/2017 | Maritan |
| 9,872,961 B2 | 1/2018 | Fourt et al. |
| 10,118,001 B2 | 11/2018 | Fourt et al. |
| 10,314,981 B2 | 6/2019 | Sampson et al. |
| 10,350,362 B2 | 7/2019 | Dennis, Jr. et al. |
| 10,363,377 B2 | 7/2019 | Atterbury et al. |
| 10,420,898 B2 | 9/2019 | Daniel |
| 10,569,019 B2 | 2/2020 | Hirschel et al. |
| 10,799,647 B2 | 10/2020 | Hostettler et al. |
| 10,888,668 B2 | 1/2021 | Mosebach et al. |
| 10,918,811 B2 | 2/2021 | Mosebach et al. |
| 10,926,032 B2 | 2/2021 | Mosebach et al. |
| 11,298,462 B2 | 4/2022 | Atterbury et al. |
| 11,357,922 B2 | 6/2022 | Mosebach et al. |
| 11,383,044 B2 | 7/2022 | Tschirren et al. |
| 11,400,232 B2 | 8/2022 | Schader et al. |
| 11,452,821 B2 | 9/2022 | LaFever et al. |
| 11,654,246 B2 | 5/2023 | Revellat et al. |
| 12,102,812 B2 | 10/2024 | Mosebach et al. |
| 12,156,994 B2 | 12/2024 | Mosebach et al. |
| 12,179,000 B2 | 12/2024 | Mosebach et al. |
| 2002/0188247 A1 | 12/2002 | Peery |
| 2004/0039336 A1 | 2/2004 | Amark et al. |
| 2004/0210199 A1 | 10/2004 | Atterbury et al. |
| 2005/0027255 A1 | 2/2005 | Lavi et al. |
| 2005/0038392 A1 | 2/2005 | DeSalvo |
| 2005/0101919 A1 | 5/2005 | Brunnberg |
| 2007/0088248 A1 | 4/2007 | Glenn et al. |
| 2008/0021373 A1 | 1/2008 | Rosati |
| 2008/0269692 A1 | 10/2008 | James et al. |
| 2010/0198182 A1 | 8/2010 | Lanigan et al. |
| 2011/0026721 A1 | 2/2011 | Parker |
| 2011/0054414 A1 | 3/2011 | Shang et al. |
| 2011/0105952 A1 | 5/2011 | Bernstein et al. |
| 2011/0238014 A1 | 9/2011 | Maritan |
| 2013/0023749 A1 | 1/2013 | Afanasewicz et al. |
| 2013/0090605 A1 | 4/2013 | O'Connor et al. |
| 2013/0131595 A1 | 5/2013 | Ekman et al. |
| 2013/0211330 A1 | 8/2013 | Pedersen et al. |
| 2013/0317427 A1 | 11/2013 | Brereton et al. |
| 2013/0324925 A1* | 12/2013 | Brereton ................ A61M 5/46 604/110 |
| 2013/0324939 A1 | 12/2013 | Brereton et al. |
| 2013/0345642 A1 | 12/2013 | Cowe |
| 2014/0114250 A1 | 4/2014 | DeSalvo et al. |
| 2014/0243751 A1 | 8/2014 | Brereton et al. |
| 2014/0243757 A1 | 8/2014 | Dasbach et al. |
| 2014/0276568 A1 | 9/2014 | Worden et al. |
| 2014/0343527 A1 | 11/2014 | Scarpine et al. |
| 2015/0265772 A1 | 9/2015 | Maritan |
| 2015/0320939 A1 | 11/2015 | Beek et al. |
| 2016/0008541 A1 | 1/2016 | Hirschel et al. |
| 2016/0008542 A1 | 1/2016 | Hirschel et al. |
| 2016/0015899 A1 | 1/2016 | Plumptre et al. |
| 2016/0144133 A1 | 5/2016 | Kemp |
| 2016/0361503 A1 | 12/2016 | Bendek et al. |
| 2017/0136173 A1 | 5/2017 | Melander et al. |
| 2018/0064875 A1 | 3/2018 | Holmqvist |
| 2018/0154078 A1 | 6/2018 | Mosebach et al. |
| 2018/0154085 A1 | 6/2018 | Mosebach et al. |
| 2018/0154089 A1 | 6/2018 | Mosebach et al. |
| 2018/0169342 A1 | 6/2018 | Mosebach et al. |
| 2019/0374717 A1 | 12/2019 | Swanson et al. |
| 2020/0289764 A1 | 9/2020 | Revellat et al. |
| 2021/0093790 A1 | 4/2021 | Mosebach et al. |
| 2021/0128837 A1 | 5/2021 | Mosebach et al. |
| 2021/0170115 A1 | 6/2021 | Mosebach et al. |
| 2021/0369966 A1 | 12/2021 | Schader et al. |
| 2022/0257865 A1 | 8/2022 | Mosebach et al. |
| 2022/0305206 A1 | 9/2022 | Schader et al. |
| 2023/0277777 A1 | 9/2023 | Revellat et al. |
| 2024/0416051 A1 | 12/2024 | Mosebach et al. |

FOREIGN PATENT DOCUMENTS

| | | |
|---|---|---|
| CN | 201111673 Y | 9/2008 |
| CN | 201243374 Y | 5/2009 |
| CN | 102209564 A | 10/2011 |
| CN | 102665801 A | 9/2012 |
| CN | 102842236 A | 12/2012 |
| CN | 202887394 U | 4/2013 |
| CN | 103177716 A | 6/2013 |
| CN | 103235538 A | 8/2013 |
| CN | 103974733 A | 8/2014 |
| CN | 104023769 A | 9/2014 |
| CN | 104080499 A | 10/2014 |
| CN | 104519929 A | 4/2015 |
| CN | 105188809 A | 12/2015 |
| CN | 105327432 A | 2/2016 |
| CN | 105451792 A | 3/2016 |
| CN | 106573114 A | 4/2017 |
| DE | 7833454 U1 | 5/1979 |
| DE | 3935672 A1 | 11/1990 |
| EP | 2583705 A1 | 4/2013 |
| EP | 2722065 A1 | 4/2014 |
| EP | 2727617 A1 | 5/2014 |
| EP | 2823841 A1 | 1/2015 |
| EP | 2868338 A1 | 5/2015 |
| EP | 3302632 A1 | 9/2020 |
| JP | H05-508098 A | 11/1993 |
| JP | H06-190041 A | 7/1994 |
| JP | H07-509636 A | 10/1995 |
| JP | 2005-508205 A | 3/2005 |
| JP | 2011-519712 A | 7/2011 |
| JP | 2012-504006 A | 2/2012 |
| JP | 2013-526894 A | 6/2013 |
| JP | 2013-526904 A | 6/2013 |
| JP | 2013-146600 A | 8/2013 |
| JP | 2013-534164 A | 9/2013 |
| JP | 2014-526298 A | 10/2014 |
| JP | 2014-531961 A | 12/2014 |
| JP | 2015-526215 A | 9/2015 |
| JP | 2015-536184 A | 12/2015 |
| JP | 2016-512766 A | 5/2016 |
| JP | 2016-513507 A | 5/2016 |
| JP | 2016-526460 A | 9/2016 |
| JP | 2016-534790 A | 11/2016 |

(56) References Cited

FOREIGN PATENT DOCUMENTS

| | | | |
|---|---|---|---|
| RU | 2140794 C1 | 11/1999 | |
| RU | 2012137269 A | 3/2014 | |
| WO | WO 1992/017223 A1 | 10/1992 | |
| WO | WO 1994/003222 A2 | 2/1994 | |
| WO | WO 2002/047746 A1 | 6/2002 | |
| WO | WO 2002/092153 A2 | 11/2002 | |
| WO | WO 2005/046773 A1 | 5/2005 | |
| WO | WO 2006/079481 A1 | 8/2006 | |
| WO | WO 2009/140251 A2 | 11/2009 | |
| WO | WO 2010/035057 A1 | 4/2010 | |
| WO | WO 2010/136077 A1 | 12/2010 | |
| WO | WO 2011/043714 A1 | 4/2011 | |
| WO | WO 2011/079278 A1 | 6/2011 | |
| WO | WO 2011/109205 A2 | 9/2011 | |
| WO | WO 2011/123024 A1 | 10/2011 | |
| WO | WO 2012/022810 A2 | 2/2012 | |
| WO | WO-2012045350 A1 * | 4/2012 | .......... A61M 5/2033 |
| WO | WO 2013/034984 A2 | 3/2013 | |
| WO | WO 2013/034985 A2 | 3/2013 | |
| WO | WO 2013/050474 A1 | 4/2013 | |
| WO | WO 2013/057032 A1 | 4/2013 | |
| WO | WO 2013/057033 A1 | 4/2013 | |
| WO | WO 2013/057034 A1 | 4/2013 | |
| WO | WO 2014/005808 A1 | 1/2014 | |
| WO | WO 2014/033141 A1 | 3/2014 | |
| WO | WO 2014/066461 A1 | 5/2014 | |
| WO | WO 2014/139914 A1 | 9/2014 | |
| WO | WO 2014/139922 A1 | 9/2014 | |
| WO | WO 2014/146209 A1 | 9/2014 | |
| WO | WO 2014/164943 A1 | 10/2014 | |
| WO | WO 2015/004049 A1 | 1/2015 | |
| WO | WO 2015/004050 A1 | 1/2015 | |
| WO | WO 2015/019071 A1 | 2/2015 | |
| WO | WO 2015/052224 A1 | 4/2015 | |
| WO | WO 2015/062915 A1 | 5/2015 | |
| WO | WO 2015/074976 A1 | 5/2015 | |
| WO | WO 2016/001304 A1 | 1/2016 | |
| WO | WO 2016/193343 A1 | 12/2016 | |
| WO | WO 2016/193344 A1 | 12/2016 | |
| WO | WO 2016/193346 A1 | 12/2016 | |
| WO | WO 2019/074788 A1 | 4/2019 | |
| WO | WO 2020/190529 A1 | 9/2020 | |

OTHER PUBLICATIONS

U.S. Appl. No. 16/759,789, filed Apr. 28, 2020, Schader et al.
Engineers Edge, "Transducers USA Announced Improved TRIP60 Series of Audio Alerts," Engineering and Technology News, Aug. 2007, 3 pages.
International Preliminary Report on Patentability in International Appln. No. PCT/EP2016/062455, mailed on Dec. 5, 2017, 7 pages.
International Preliminary Report on Patentability in International Appln. No. PCT/EP2016/062449, mailed on Dec. 14, 2017, 7 pages.
International Preliminary Report on Patentability in International Appln. No. PCT/EP2016/062450, mailed on Dec. 14, 2017, 9 pages.
International Preliminary Report on Patentability in International Appln. No. PCT/EP2016/062452, mailed on Dec. 14, 2017, 8 pages.
International Preliminary Report on Patentability in International Appln. No. PCT/EP2016/062454, mailed on Dec. 14, 2017, 8 pages.
International Preliminary Report on Patentability in International Appln. No. PCT/EP2018/079915, mailed on May 14, 2020, 9 pages.
International Preliminary Report on Patentability in International Appln. No. PCT/EP2018/079917, mailed on May 14, 2020, 9 pages.
International Search Report and Written Opinion in International Appln. No. PCT/EP2016/062455, mailed on Sep. 27, 2016, 9 pages.
International Search Report and Written Opinion in International Appln. No. PCT/EP2016/062449, mailed on Aug. 17, 2016, 8 pages.
International Search Report and Written Opinion in International Appln. No. PCT/EP2016/062450, mailed on Aug. 5, 2016, 9 pages.
International Search Report and Written Opinion in International Appln. No. PCT/EP2016/062452, mailed on Sep. 15, 2016, 11 pages.
International Search Report and Written Opinion in International Appln. No. PCT/EP2016/062454, mailed on Aug. 5, 2016, 9 pages.
International Search Report and Written Opinion in International Appln. No. PCT/EP2018/079915, mailed on Dec. 5, 2018, 10 pages.
International Search Report and Written Opinion in International Appln. No. PCT/EP2018/079917, mailed on Dec. 5, 2018, 10 pages.
Karpova, "The basics of surdopedagogy," Ekaterinburg, pp. 20-21, 2008, 7 pages (with machine translation).
National Standards of People's Republic of China, "Audible and/or Visual Fire Alarm Signaling Appliances", General Administration of Quality Supervision, Inspection and Quarantine of the People's Republic of China, Jul. 2011, 39 pages (with machine translation).
National Standards of People's Republic of China, "Fire Detection and Alarm Systems-Smoke Alarms", General Administration of Quality Supervision, Inspection and Quarantine of the People's Republic of China, Jul. 2006, 45 pages (with machine translation).
National Standards of People's Republic of China, "Vehicle Electronic Sirens", General Administration of Quality Supervision, Inspection and Quarantine of the People's Republic of China, Dec. 2014, 31 pages (with machine translation).

* cited by examiner

DRUG DELIVERY DEVICE WITH FEEDBACK MECHANISM

CROSS REFERENCE TO RELATED APPLICATIONS

The present application is a continuation of U.S. patent application Ser. No. 18/968,712, filed Dec. 4, 2024, which is a continuation of U.S. patent application Ser. No. 17/172,602, filed Feb. 10, 2021, now U.S. Pat. No. 12,186,540, which is a continuation of U.S. patent application Ser. No. 15/578,668, filed Nov. 30, 2017, now U.S. Pat. No. 10,940,270, which is the national stage entry of International Patent Application No. PCT/EP2016/062455, filed on Jun. 2, 2016, and claims priority to Application No. EP 15170590.2, filed on Jun. 3, 2015, the disclosures of which are expressly incorporated herein in entirety by reference thereto.

TECHNICAL FIELD

The disclosure relates to a drug delivery device.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by a plunger which is continuously pressed during the injection. There are numerous disadvantages associated with this approach. For example, if the plunger is released prematurely, the injection will stop and may not deliver an intended dose. Furthermore, the force required to push the plunger may be too high (e.g., if the user is elderly or a child). And, aligning the injection device, administering the injection, and keeping the injection device still during the injection may require dexterity which some patients may not have.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

Furthermore, it is desirable to administer the full dose in order to achieve full effectiveness of the medicament within the patient.

Thus, there remains a need for an improved drug delivery device.

SUMMARY

Certain aspects of the present disclosure can be implemented to provide an improved drug delivery device.

Certain aspects of the present disclosure can be implemented as a drug delivery device according to claim 1.

Exemplary embodiments of the disclosure are given in the dependent claims.

According to the disclosure, a drug delivery device comprises:
- a case adapted to enclose a medicament container,
- a plunger disposed within the case and slidable from a proximal position into a distal position for delivering a medicament from the medicament container,
- at least one feedback mechanism activated by movement of the plunger, the feedback mechanism comprising a collar, a control spring biasing the collar in a distal direction, a needle shroud that operatively couples to the collar in a first state, the needle shroud prevented from decoupling the collar by the plunger being in the proximal position, wherein the plunger, during movement from the proximal position towards the distal position, is adapted to allow decoupling of the needle shroud from the collar, to allow a movement of the collar relative to the needle shroud until the collar couples to the needle shroud in a second state.

The drug delivery device is improved due to the feedback mechanism used for indicating to a patient or user that the full dose of medicament was spent.

In an exemplary embodiment the needle shroud axially couples to the collar in the first state and in the second state.

In an exemplary embodiment, the collar comprises one or more resilient first snap-fit joints adapted to couple to the needle shroud in a ramp engagement in the first state, the first snap-fit joints adapted to inwardly deflect due to this ramp engagement, wherein the plunger in the proximal position is adapted to inwardly support the first snap-fit joints, preventing their inward deflection and wherein the plunger in the distal position is axially removed from the snap-fit joints, allowing their inward deflection.

In an exemplary embodiment, the collar comprises one or more third collar ribs adapted to couple to the needle shroud in the second state.

In an exemplary embodiment, the needle shroud comprises one or more openings adapted to allow the deflected first snap-fit joints to engage within the openings.

In an exemplary embodiment, the control spring is arranged as a compression spring configured to surround at least part of the collar.

In an exemplary embodiment, the control spring is proximally grounded in the case.

In an exemplary embodiment, the drug delivery device further comprises a plunger release mechanism adapted for preventing release of the plunger when the needle shroud is in a distal position and adapted to release the plunger when the needle shroud is in a proximal position.

In an exemplary embodiment, the plunger release mechanism comprises an angled surface on the case and a rib on the plunger adapted to engage the angled surface so that when a force in the distal direction is applied to the plunger, the rib abuts the angled surface biasing the rib and the plunger in a rotational direction, wherein the collar is adapted to rotationally support the rib, preventing it from moving in the rotational direction when the needle shroud is in the distal position and wherein the collar is adapted to be removed from the rib, allowing it to move in the rotational direction.

In an exemplary embodiment, an inner rib is arranged on the case adapted to rotationally support the collar, preventing it from moving in the rotational direction.

In an exemplary embodiment, the drug delivery device further comprises a shroud lock mechanism adapted to lock the collar in an advanced position.

In an exemplary embodiment, the shroud lock mechanism comprises one or more resilient second snap-fit joints on the collar adapted to engage in a respective opening in the case, wherein the opening comprises an axial extension allowing for some free travel of the snap-fit joints, wherein the second snap-fit joints comprise a respective angled surface adapted to be deflected by ends of the opening for disengaging the opening, wherein a transversal proximal surface on the second snap-fit joint is adapted to proximally abut the case, preventing the collar from moving in the proximal direction.

In an exemplary embodiment, the case comprises a front case and a rear case adapted to be coupled to each other.

In an exemplary embodiment, the front case is part of a control subassembly, which further comprises the needle shroud and a cap, wherein the rear case is part of a drive subassembly, which further comprises the plunger, a drive spring for biasing the plunger in the distal direction, the control spring and the collar.

In an exemplary embodiment, the plunger is hollow and the drive spring is arranged within the plunger.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

Figure 1:
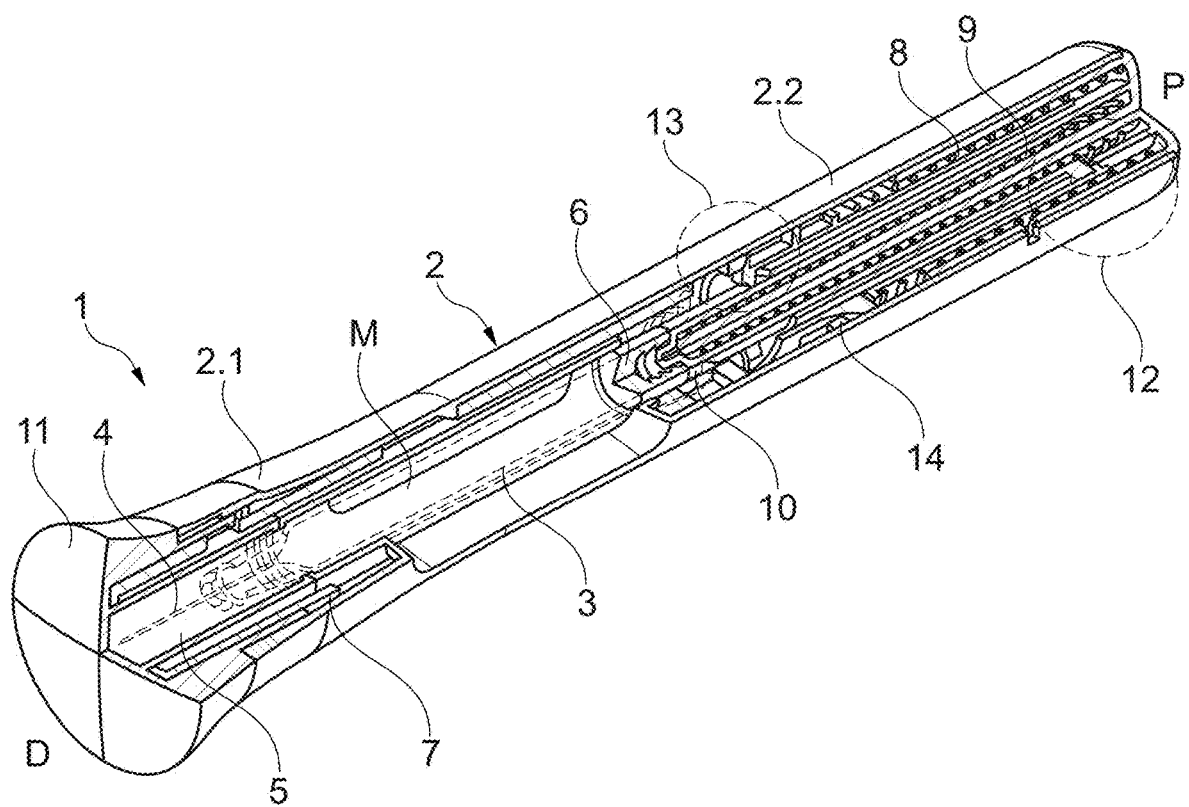
FIG. 1 is a perspective view of an exemplary embodiment of an auto-injector.

FIG. 1 is a perspective view of an exemplary embodiment of an auto-injector 1. The auto-injector 1 comprises a case 2 comprising a sleeve shaped front case 2.1 and a rear case 2.2. A cap 11 is attached at a distal end of the case 2. A sleeve-shaped needle shroud 7 is telescoped within the case 2. The case 2 is adapted to receive a medicament container 3, such as a syringe 3, for example a glass syringe. The medicament container is referred to hereinafter as the "syringe 3". The syringe 3 may be a pre-filled syringe containing a medicament M and having a needle 4 arranged at a distal end of the syringe 3. In another exemplary embodiment, the medicament container 3 may be a cartridge which includes the medicament M and engages a removable needle (e.g., by threads, snaps, friction, etc.) When the auto-injector 1 or the syringe 3 is assembled, a protective needle sheath 5 is attached to the needle 4. A stopper 6 is arranged for sealing the syringe 3 proximally and for displacing a liquid medicament M contained in the syringe 3 through the hollow needle 4. The syringe 3 is held in the case 2 and supported at its proximal end therein.

The protective needle sheath 5 may be coupled to the cap 11 so that when the cap 11 is removed, the protective needle sheath 5 is also removed from the needle 4. The cap 11 may comprise grip features for facilitating removal of the cap 11.

The sleeve-shaped needle shroud 7 is telescoped in the distal end of the case 2. A control spring 8 is arranged to bias the needle shroud 7 in a distal direction D against the case 2.

A drive spring 9 in the shape of a compression spring is arranged within a proximal part of the case 2. A plunger 10 serves for forwarding the force of the drive spring 9 to the stopper 6. In an exemplary embodiment, the plunger 10 is hollow and the drive spring 9 is arranged within the plunger 10, biasing the plunger 10 in the distal direction D against the rear case 2.2.

The auto-injector 1 may be divided in two subassemblies, a control subassembly 1.1 and a drive subassembly 1.2. This allows for improving flexibility as to the time and location of manufacture of the subassemblies 1.1, 1.2 and final assembly with the syringe 3.

Figure 2:
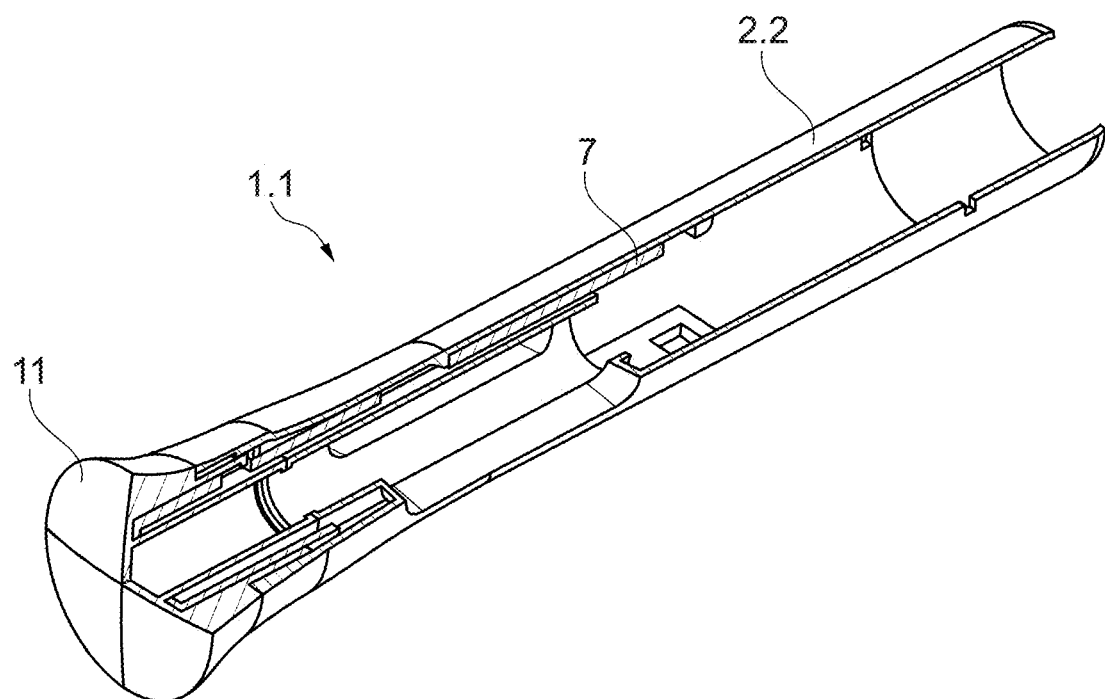
FIG. 2 is a perspective view of a control subassembly.
Figure 3:
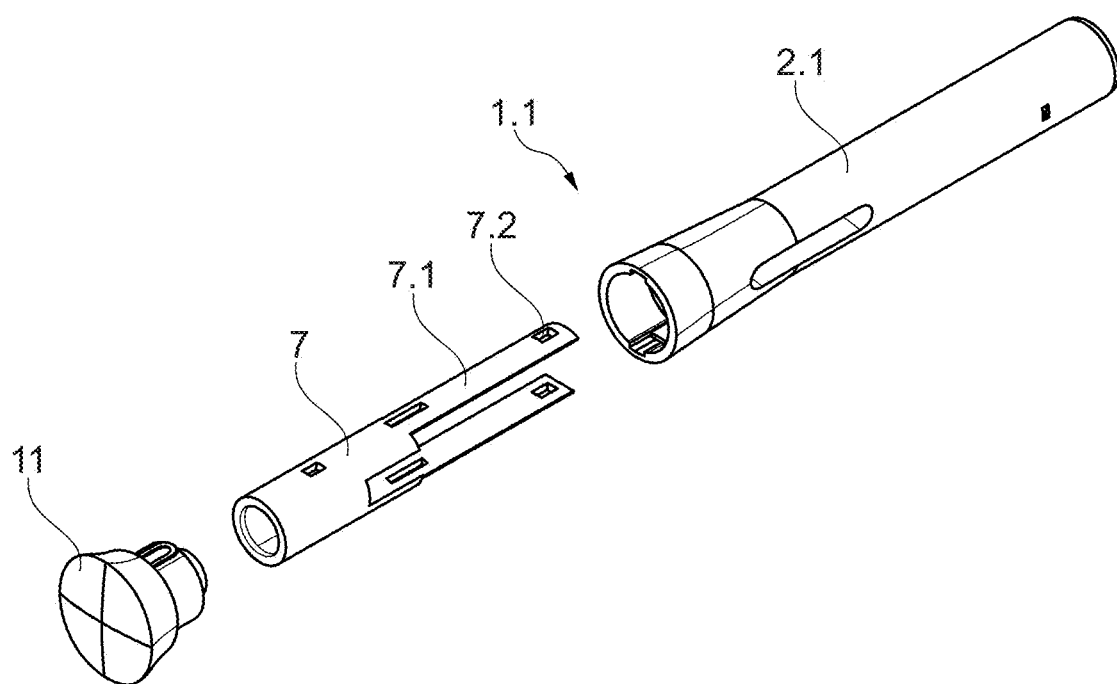
FIG. 3 is a perspective exploded view of the control subassembly.

FIG. 2 is a perspective view of the control subassembly 1.1. FIG. 3 is a perspective exploded view of the control subassembly 1.1. The control subassembly 1.1 comprises all parts and mechanisms which control access to the needle 4 and the forces a user will feel when they use the auto-injector 1. The control subassembly 1.1 comprises the cap 11, the needle shroud 7 and the front case 2.1.

Figure 4:
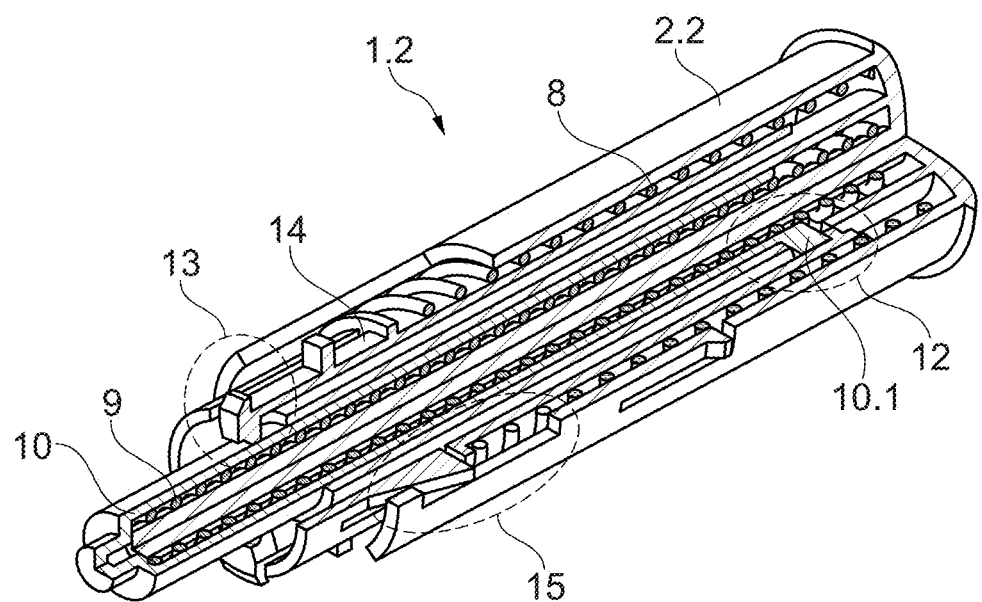
FIG. 4 is a perspective view of a drive subassembly.
Figure 5:
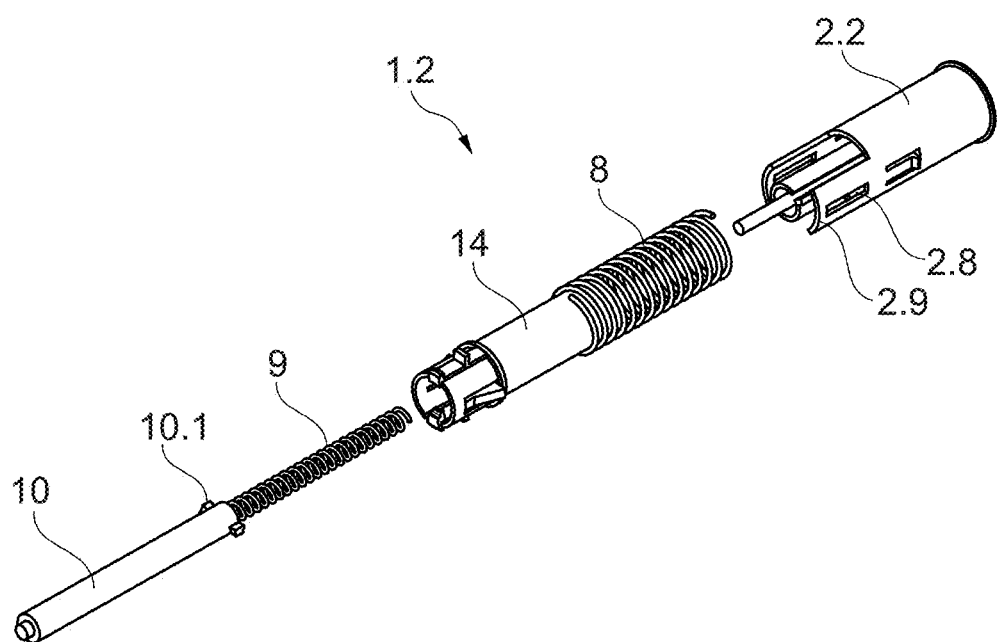
FIG. 5 is a perspective exploded view of the drive subassembly.

FIG. 4 is a perspective view of the drive subassembly 1.2. FIG. 5 is a perspective exploded view of the drive subassembly 1.2. The drive subassembly 1.2 comprises the components required to deliver the medicament M. If the viscosity or volume of the medicament M in the syringe 3 is varied, only parts of the drive subassembly 1.2 may need to be changed. The drive subassembly 1.2 comprises the plunger 10, the drive spring 9, the rear case 2.2, the control spring 8 and a sleeve shaped collar 14 which will be explained in more detail below.

Figure 6:
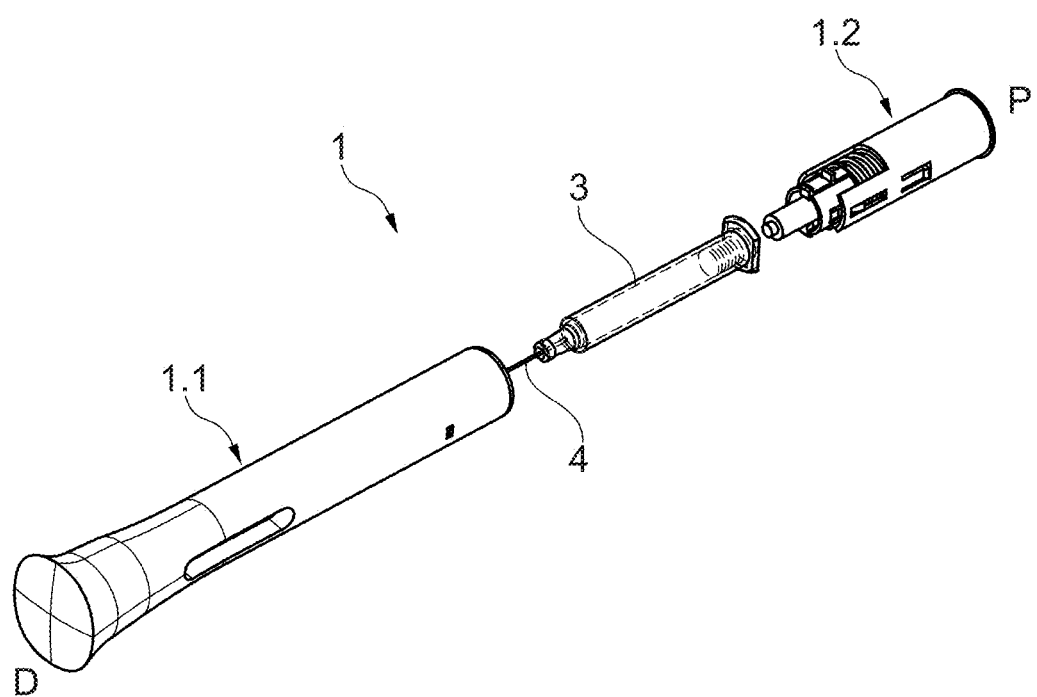
FIG. 6 is a schematic exploded view of the auto-injector during assembly.

FIG. 6 is a schematic exploded view of the auto-injector 1 during assembly. In order to assemble the auto-injector 1, a syringe 3 with an attached needle 4 and a protective needle sheath (not illustrated) is inserted into the control subassembly 1.1 in the distal direction D. Afterwards, the drive subassembly 1.2 is inserted into the control subassembly 1.1 in the distal direction D.

A plunger release mechanism 12 is schematically illustrated in four different states in FIGS. 7A to 7D. The plunger release mechanism 12 is arranged for preventing release of the plunger 10 prior to depression of the needle shroud 7 and for releasing the plunger 10 once the needle shroud 7 is sufficiently depressed.

The plunger release mechanism 12 is adapted to control the automated activation of syringe emptying. The plunger release mechanism 12 is activated immediately prior to full needle insertion. The plunger release mechanism 12 comprises the plunger 10, a longitudinal inner rib 2.3 on the rear case 2.2 and the collar 14. The needle shroud 7, not represented in FIGS. 7A to 7D, is coupled to the collar 14 and adapted to push the collar 14 in a proximal direction P.

The needle shroud 7, the rear case 2.2 and its inner rib 2.3, and the collar 14 are configured to move only in an axial direction, i.e. in the distal direction D and the proximal direction P, whereas the plunger 10 can both move rotationally in rotational directions R1, R2 and axially in the distal direction D and the proximal direction P. In an exemplary embodiment, there may be no compliant part in the plunger release mechanism 12, i.e. the parts may be all rigid and move as a whole with no relative deformation within a part.

Figure 7A:
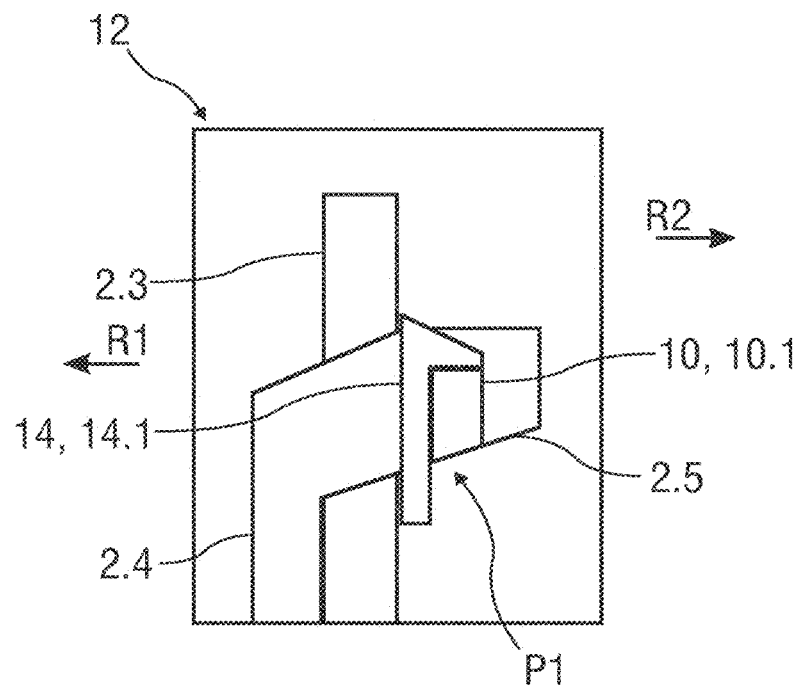
FIG. 7A is a schematic view of a plunger release mechanism in a pre-assembly or pre-use state.

FIG. 7A shows the plunger release mechanism 12 in a pre-assembly or pre-use state with the plunger 10 in a proximal position P1. The configuration of the plunger release mechanism 12 does not change when transitioning from the pre-assembly state to the pre-use state, i.e. assembling the control sub-assembly 1.1 and the drive sub-assembly 1.2 does not impact the plunger release mechanism 12.

In the pre-assembly or pre-use state, a rib 10.1 on the plunger 10 is slid in an opening 2.4 within the rear case 2.2. The opening 2.4 has an angled surface 2.5 so that when a force in the distal direction D is applied to the plunger 10, e.g. by the drive spring 9, the rib 10.1 abuts the angled surface 2.5 and the plunger 10 attempts to rotate in the rotational direction R1. The rib 10.1 is prevented to move along the angled surface 2.5 of the opening 2.4 by a first collar rib 14.1 on the collar 14. The collar 14 is prevented from rotating in the rotational direction R1 by the inner rib 2.3 on the rear case 2.2.

Figure 7B:
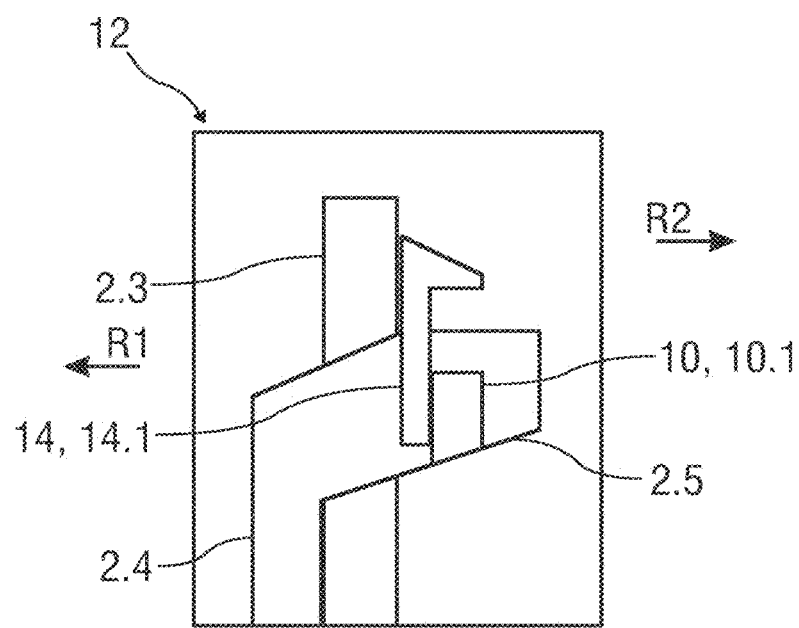
FIG. 7B is a schematic view of the plunger release mechanism in a state during extension of an injection needle.

FIG. 7B shows the plunger release mechanism 12 in a state during extension of the injection needle 4. The needle shroud 7 is moved in the proximal direction P into the front case 2.1, e.g. by a user pressing the shroud against an injection site, thereby inserting the needle 4 into the injection site. As the needle shroud 7 is coupled to the collar 14, the collar 14 moves in the proximal direction P as well. The first collar rib 14.1 moves in the proximal direction P accordingly, beginning to clear the way for the rib 10.1 of the plunger 10.

Figure 7C:
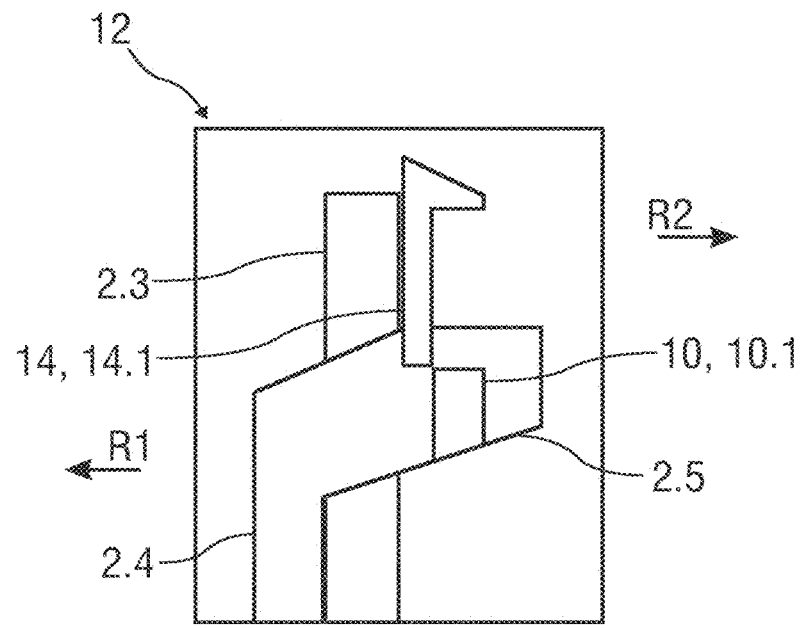
FIG. 7C is a schematic view of the plunger release mechanism in a state during extension of the injection needle immediately prior to the needle reaching full insertion depth.

FIG. 7C shows the plunger release mechanism 12 in a state during extension of the injection needle 4 immediately prior to the needle 4 reaching full insertion depth. The first collar rib 14.1 has been moved further in the proximal direction P and disengages the rib 10.1 on the plunger 10 so that the plunger 10 is no longer prevented from rotating in the rotational direction R1. The rib 10.1 on the plunger 10 is free to slide along the angled surface 2.5 of the opening 2.4 in the rear case 2.2.

Figure 7D:
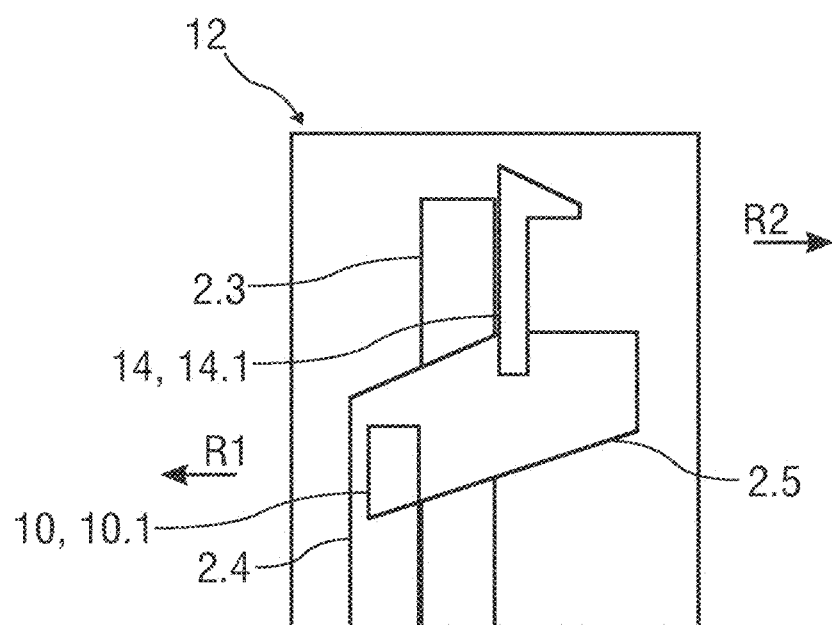
FIG. 7D is a schematic view of the plunger release mechanism a state at the beginning of an injection.

FIG. 7D shows the plunger release mechanism 12 in a state at the beginning of an injection. The rib 10.1 on the plunger 10 finishes its course along the angled surface 2.5 of the opening 2.4 in the rear case 2.2, thus becoming able to move in the distal direction D without being further rotated. Under the action of the drive spring 9, the plunger 10 pushes on the stopper 6 and starts to empty the content of the syringe 3.

A feedback mechanism 13 is arranged for enabling emission of an audible and/or tactile feedback indicating the completion of medicament delivery. The feedback mechanism 13 is schematically illustrated in six different states in FIGS. 8A to 8F.

The feedback mechanism 13 comprises the plunger 10, the rear case 2.2, the needle shroud 7, the collar 14 and the control spring 8.

Figure 8A:
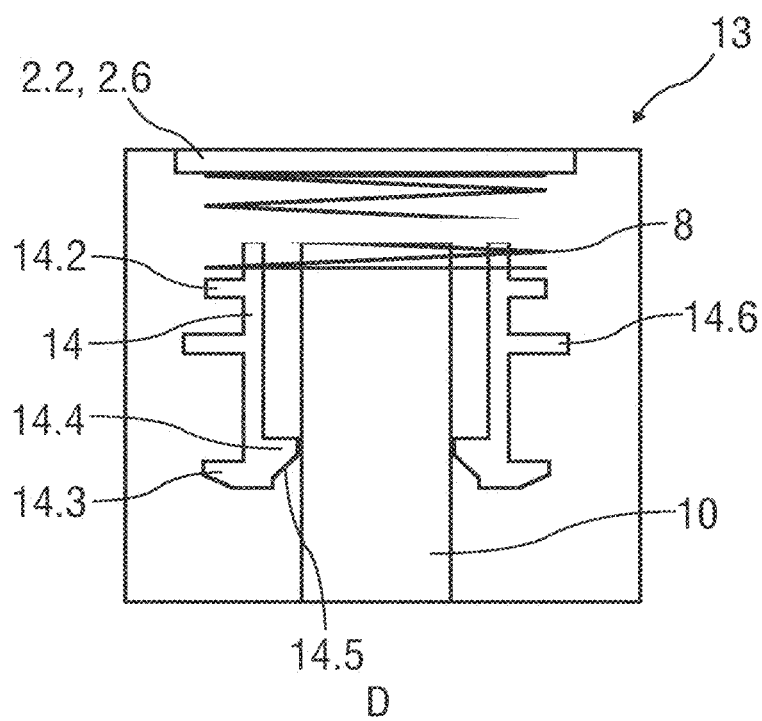
FIG. 8A is a schematic view of a feedback mechanism in the pre-assembly state.

FIG. 8A shows the feedback mechanism 13 in the pre-assembly state. Only the drive sub-assembly 1.2 is represented in this state. The control spring 8 is compressed between two second collar ribs 14.2 on the collar 14 and a proximal end 2.6 of the rear case 2.2. The plunger 10 is arranged within the collar 14 between inner protrusions 14.4 of first snap-fit joints 14.3 on the collar 14. Consequently, the first snap-fit joints 14.3 cannot deflect inward under the force of the control spring 8 pushing in the distal direction D.

Figure 8B:
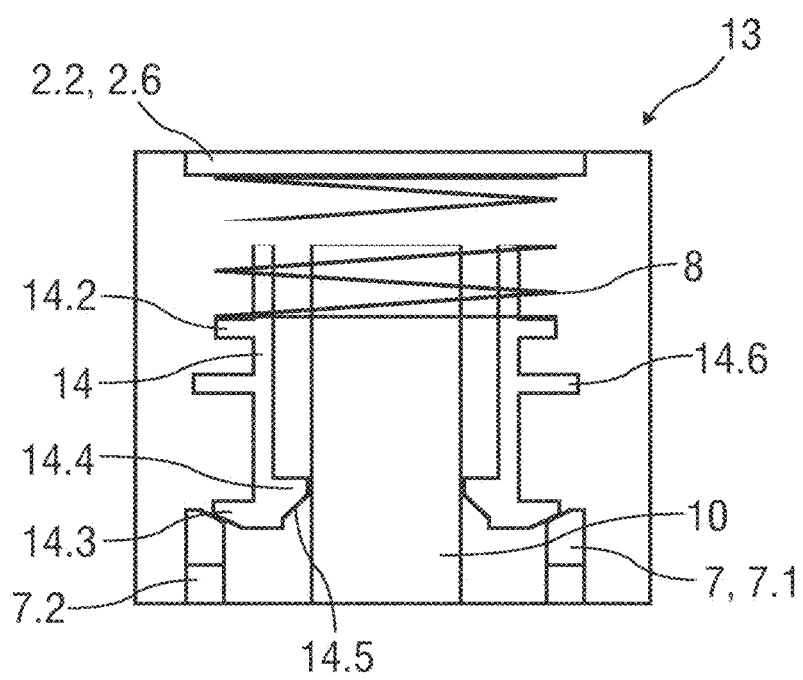
FIG. 8B is a schematic view of the feedback mechanism in the pre-use state.

FIG. 8B shows the feedback mechanism 13 in the pre-use state. The control subassembly 1.1 is pushed into the drive sub-assembly 1.2. The front case 2.1 and the rear case 2.2 may be coupled by two clips on the front case 2.1 getting caught within openings in the rear case 2.2 (not represented) or vice versa. The needle shroud 7 is inserted and proximal arms 7.1 on the needle shroud 7 axially abut the first snap-fit joints 14.3.

Figure 8C:
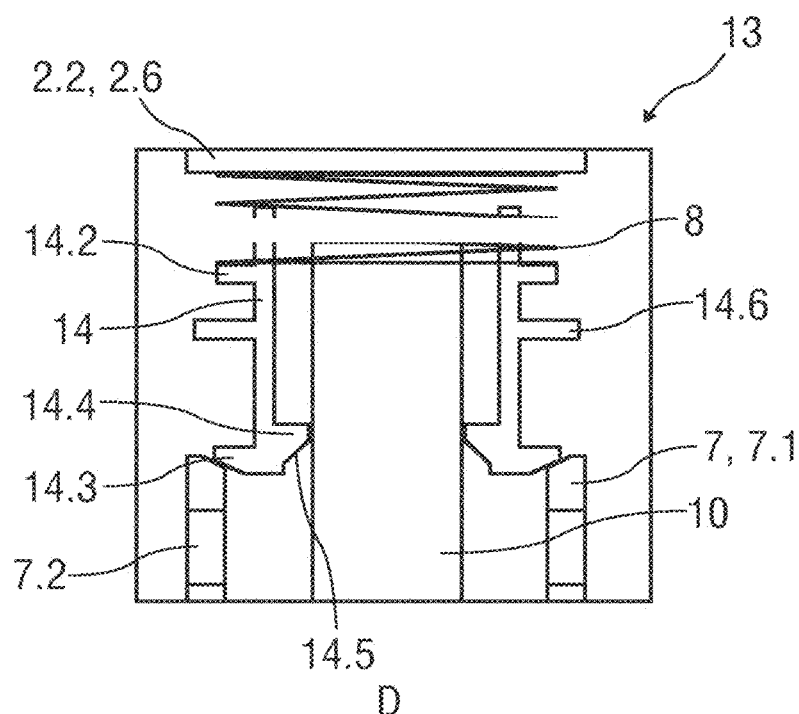
FIG. 8C is a schematic view of the feedback mechanism in a state with the needle at full insertion depth.

FIG. 8C shows the feedback mechanism 13 in a state with the needle 4 at full insertion depth. The needle shroud 7 has been fully moved in the proximal direction P, e.g. by pushing it against an injection site, and has dragged along the collar 14 in the proximal direction P, compressing the control spring 8. As the plunger 10 is arranged within the collar 14 between the inner protrusions 14.4 of the first snap-fit joints 14.3, the first snap-fit joints 14.3 cannot deflect inward under the force of the control spring 8 pushing in the distal direction D.

Figure 8D:
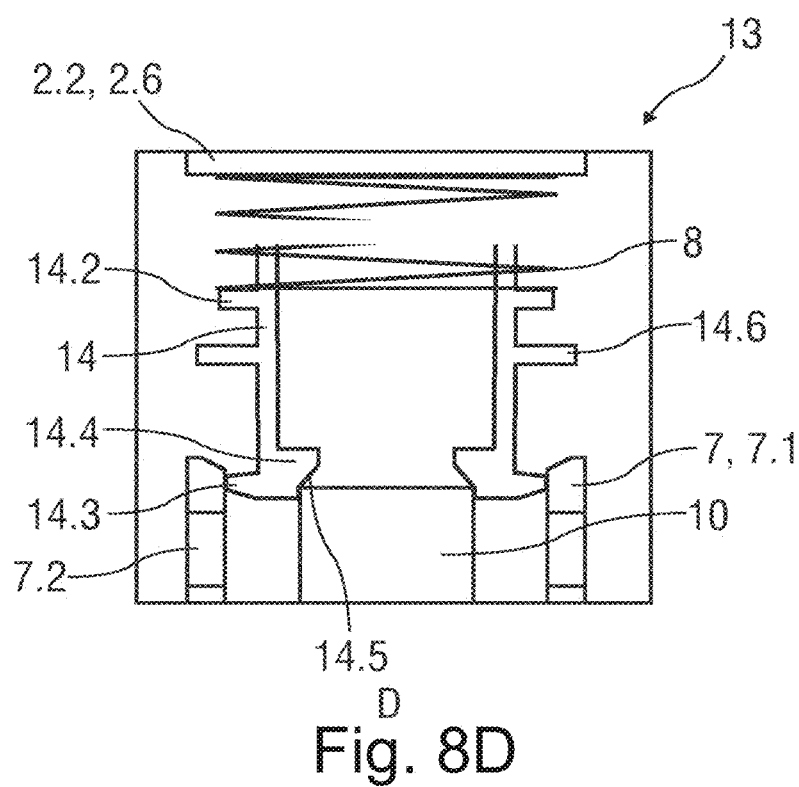
FIG. 8D is a schematic view of the feedback mechanism in a state during triggering of a feedback.

FIG. 8D shows the feedback mechanism 13 in a state when the feedback is triggered near the end of medicament dispense. The plunger 10, approaching the end of its travel with the stopper 6 having nearly bottomed out in the syringe 3, slides down inward angled surfaces 14.5 on the inner protrusions 14.4 allowing for inward deflection of the first snap-fit joints 14.3. Due to a ramp engagement between the first snap-fit joints 14.3 and the proximal ends of the proximal arms 7.1 of the collar 14, the first snap-fit joints 14.3 are inwardly deflected driven by the control spring 8 disengaging them from their axial abutment with the proximal arms 7.1, moving them between the proximal arms 7.1.

Figure 8E:
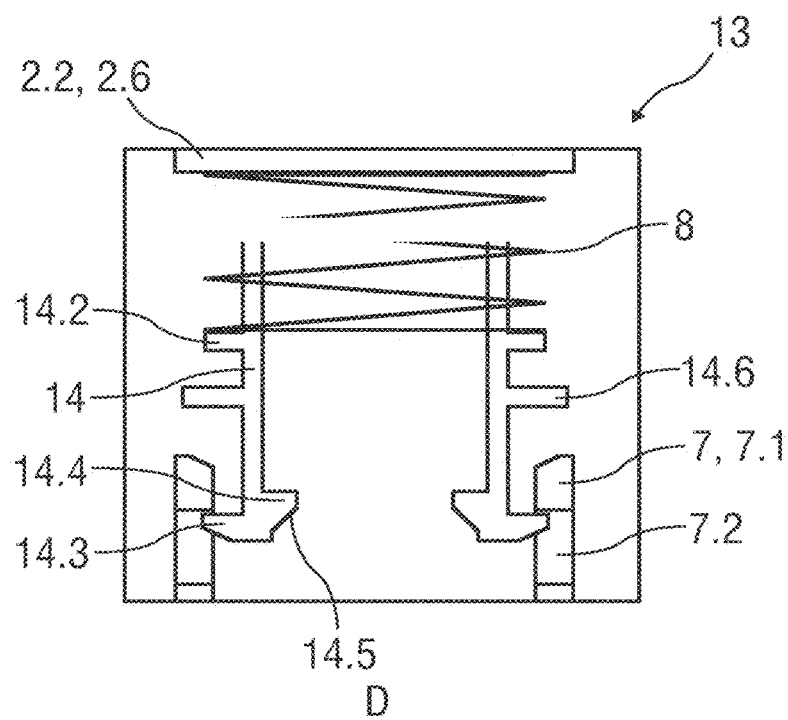
FIG. 8E is a schematic view of the feedback mechanism in a state at the end of dose prior to generating the feedback.

FIG. 8E shows the feedback mechanism 13 in a state at the end of dose prior to generating the feedback. The plunger 10 at least almost finishes emptying the syringe 3 and is completely removed from between the first snap-fit joints 14.3. In the meantime, the collar 14 has travelled further in the distal direction D along the proximal arms 7.1 and the two first snap-fit joints 14.3 have arrived at respective openings 7.2 in the proximal arms 7.1, allowing the first snap-fit joints 14.3 to relax and straighten back to their initial shape within and engage within the openings 7.2 in the proximal arms 7.1.

Figure 8F:
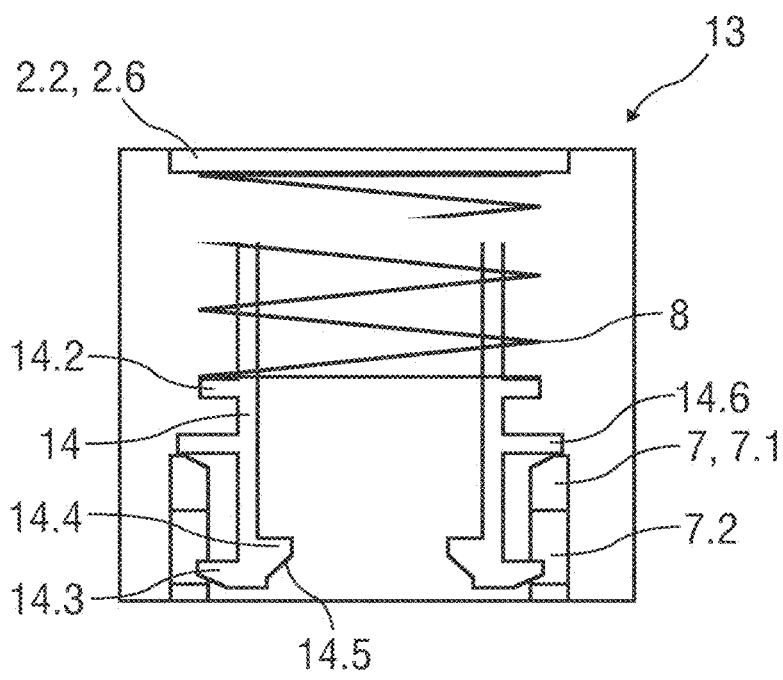
FIG. 8F is a schematic view of the feedback mechanism in a state after having generated the feedback.

FIG. 8F shows the feedback mechanism 13 in a state at the end of dose F after having generated the feedback. Due to the relaxed first snap-fit joints 14.3 being engaged within the openings 7.2 whose longitudinal extension allows for some free travel of the first snap-fit joints 14.3, the friction acting against the control spring 8 is reduced and the control spring 8 can now expand and drive the collar 14 in the distal direction D along the proximal arms 7.1 of the needle shroud 7 until two third collar ribs 14.6 on the collar 14 axially hit the proximal arms 7.1 of the needle shroud 7, thus creating an audible and/or tactile feedback which indicates that the dose is complete.

FIGS. 9A to 9D show schematic views of a shroud lock mechanism 15 in four different states. The shroud lock mechanism 15 is arranged to lock the needle shroud 7 after removal of the auto-injector 1 from an injection site post-use and consequent translation of the needle shroud 7 in the distal direction D relative the case 2.

The shroud lock mechanism 15 comprises the rear case 2.2 and the collar 14.

Figure 9A:
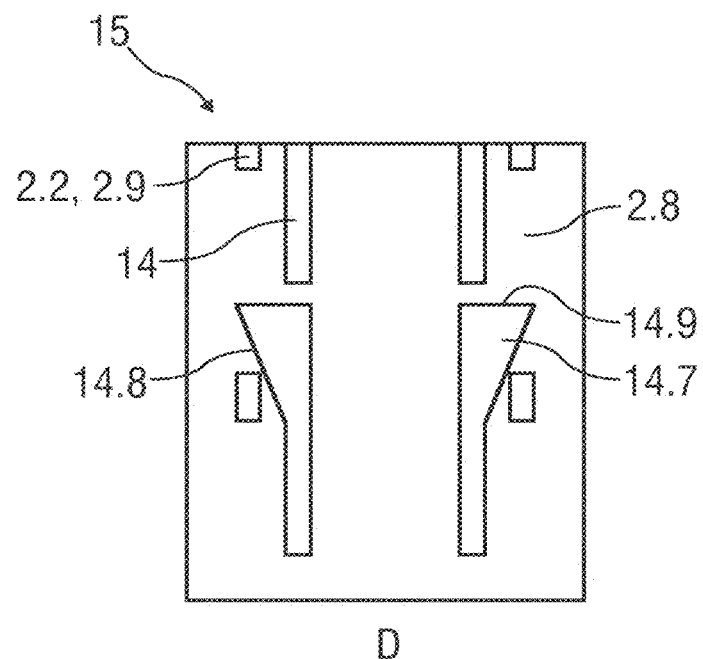
FIG. 9A is a schematic view of a shroud lock mechanism in a state prior to needle insertion, i.e. in a preassembly state or preuse state.

FIG. 9A shows the shroud lock mechanism 15 in a state prior to needle insertion, i.e. in a preassembly state or pre-use state. Two second snap-fit joints 14.7 are arranged on the collar 14 and rest in two openings 2.8 in distal arms 2.9 on the rear case 2.2.

Figure 9B:
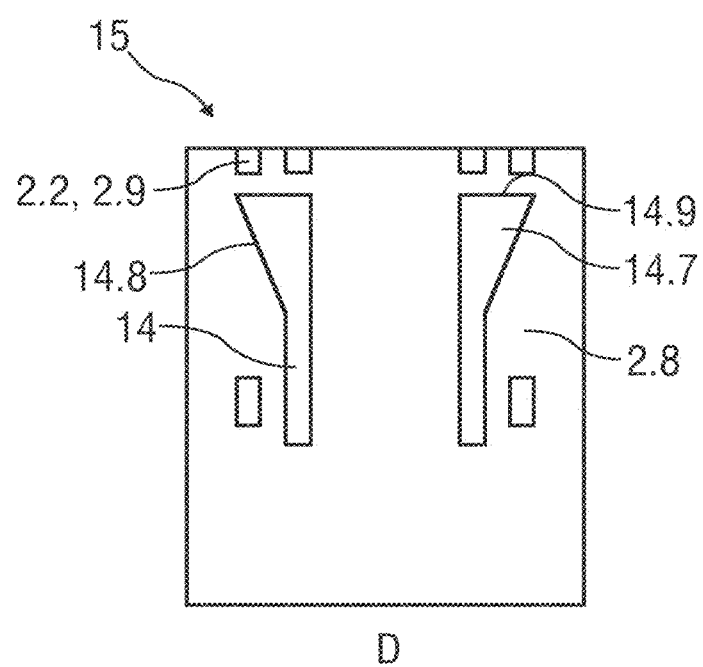
FIG. 9B is a schematic view of the shroud lock mechanism in a state between the beginning of the injection and the release of the feedback mechanism.

FIG. 9B shows the shroud lock mechanism 15 in a state between the beginning of the injection and the release of the feedback mechanism 13 (both states included). The needle shroud 7 and the collar 14 moved in the proximal direction P as the needle shroud 7 was pushed against the injection site. The two second snap-fit joints 14.7 move in the proximal direction P accordingly, travelling up the openings 2.8 whose axial extension allows for some free travel.

Figure 9C:
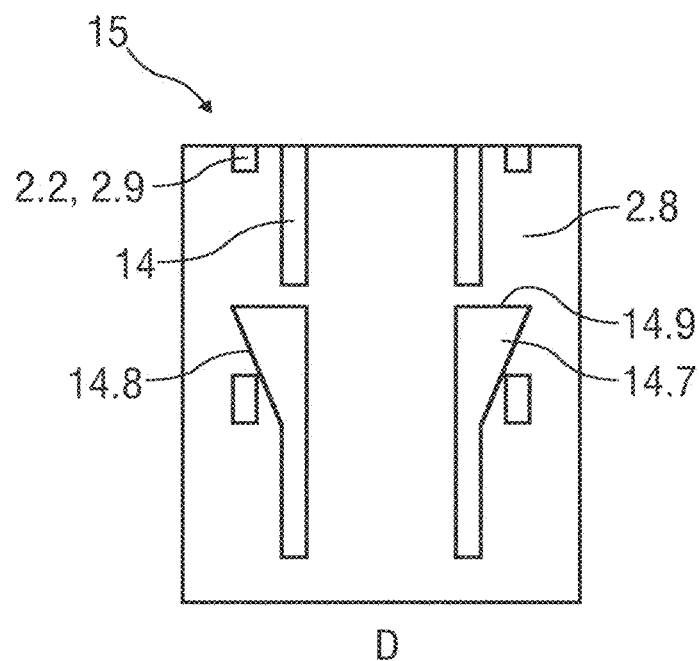
FIG. 9C is a schematic view of the shroud lock mechanism in a state at the end of dose after release of the feedback mechanism.

FIG. 9C shows the shroud lock mechanism 15 in a state at the end of dose after release of the feedback mechanism 13. As the feedback mechanism 13 is released, the collar 14 moves in the distal direction D (cf. FIG. 8F). The two second snap-fit joints 14.7 move in the distal direction D accordingly, travelling down the openings 2.8 in the distal arms 2.9 of the rear case 2.2.

Figure 9D:
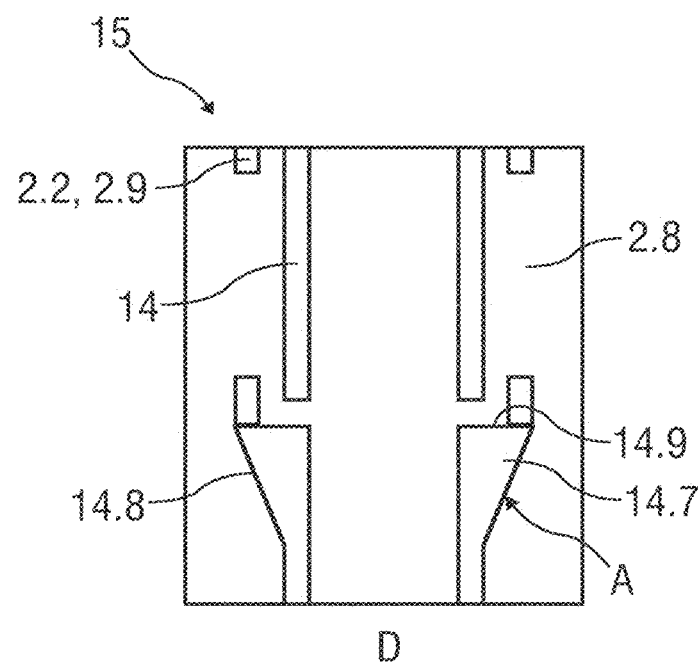
FIG. 9D is a schematic view of the shroud lock mechanism in a post-use state.

FIG. 9D shows the shroud lock mechanism 15 in a post-use state. Once the medicament injection is complete, the user pulls the auto-injector 1 away from the injection site and the needle shroud 7 is forced out of the case 2 in the distal direction D by the control spring 8, enveloping the needle 4 and thus acting as a protective shell around it (not represented). The collar 14 is arranged between the needle shroud 7 and the control spring 8. Following the motion of the needle shroud 7, the collar 14 moves in the distal direction D as well. The two second snap-fit joints 14.7 move accordingly and are deflected inward within the rear case 2.2 as angled surfaces 14.8 on the second snap-fit joints 14.7 engage the distal ends of the openings 2.8. As the second snap-fit joints 14.7 travel further beyond the distal ends of the distal arms 2.9 on the rear case 2.2, they are allowed to relax and straighten back outwards to their initial shape. The collar 14 is in an advanced position A and the needle shroud 7, coupled to the collar 14, is in its distal position S1. If it is attempted to push the needle shroud 7 in the proximal direction P again, transversal proximal surfaces 14.9 on the second snap-fit joints 14.7 proximally abut the distal arms 2.9 of the rear case 2.2 preventing further depression of the needle shroud 7 and re-exposure of the needle 4.

A sequence of operation of the auto-injector 1 is as follows:

The auto-injector 1 is initially in the state as shown in FIG. 1. The plunger release mechanism 12 is in the pre-use state as shown in FIG. 7A. The feedback mechanism 13 is in the pre-use state as illustrated in FIG. 8B. The shroud lock mechanism 15 is in the pre-use state as illustrated in FIG. 9A.

Figure 10:
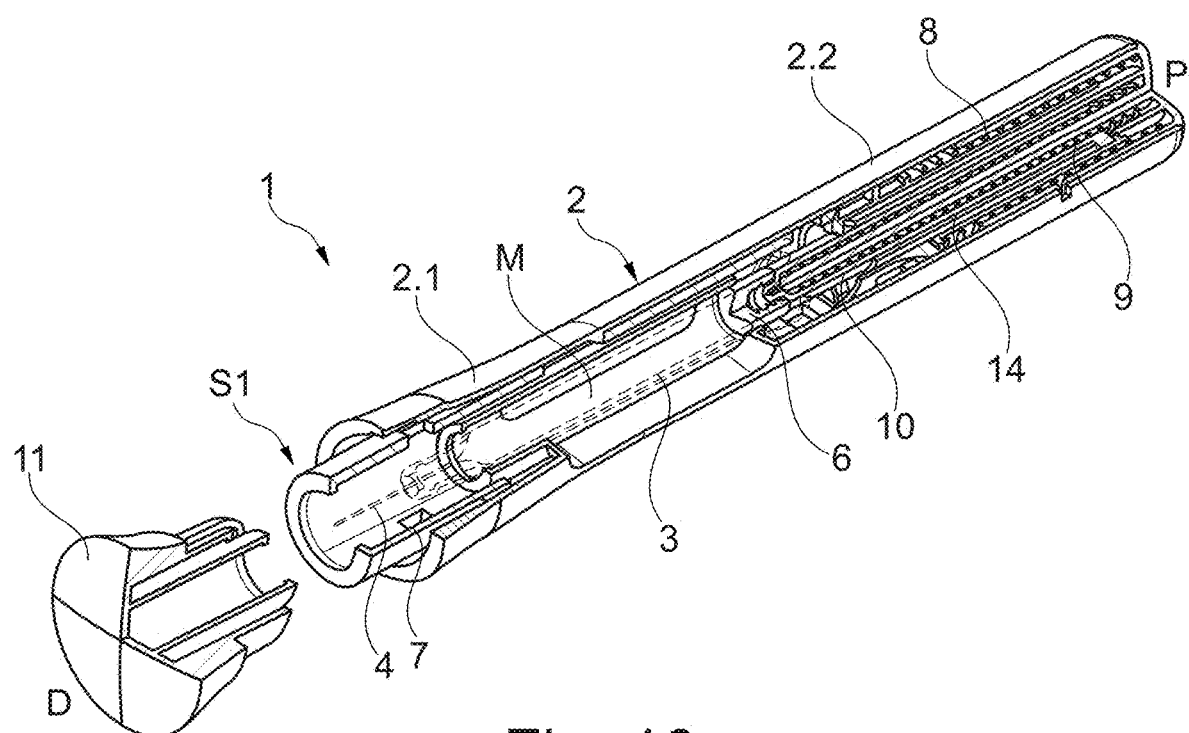
FIG. 10 is a perspective longitudinal section of the auto-injector with the cap removed.

The user removes the cap 11 pulling it in the distal direction D away from the case 2. The protective needle sheath 5 may be coupled to the cap 11 so that when the cap 11 is removed, the protective needle sheath 5 is also removed from the needle 4. FIG. 10 is a perspective longitudinal section of the auto-injector 1 with the cap 11 removed. The needle shroud 7 is in a distal position S1.

Figure 11:
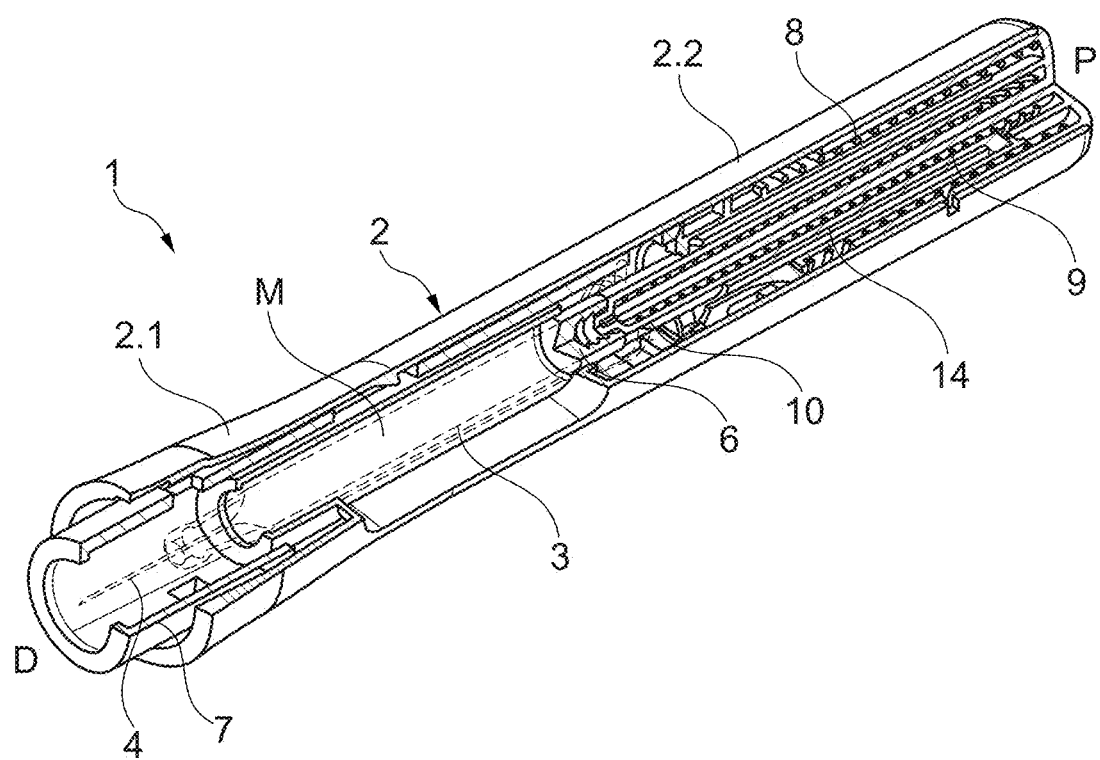
FIG. 11 is a perspective longitudinal section of the auto-injector with the needle shroud being moved in the proximal direction.

FIG. 11 is a perspective longitudinal section of the auto-injector 1 with the needle shroud 7 being moved in the proximal direction P, e.g. by placing it against the injection site and sliding the case 2 forwards. The control spring 8 is held between the collar 14 and the rear case 2.2 and is further compressed when the case 2 moves forwards relative to the needle shroud 7. Except for the needle shroud 7 and the collar 14, all components of the auto-injector 1 move with the case 2. The needle shroud 7 and the collar 14, axially coupled as shown in FIG. 8B, move in the proximal direction P in comparison to the rest of the parts of the auto-injector 1, thus initiating the plunger release mechanism 12. The plunger release mechanism 12 thus arrives in the state as illustrated in FIG. 7B. The feedback mechanism 13 transitions from the pre-use state shown in FIG. 8B to the state as illustrated in FIG. 8C. The shroud lock mechanism 15 transitions from the pre-use state of FIG. 9A to the state as illustrated in FIG. 9B.

Figure 12:
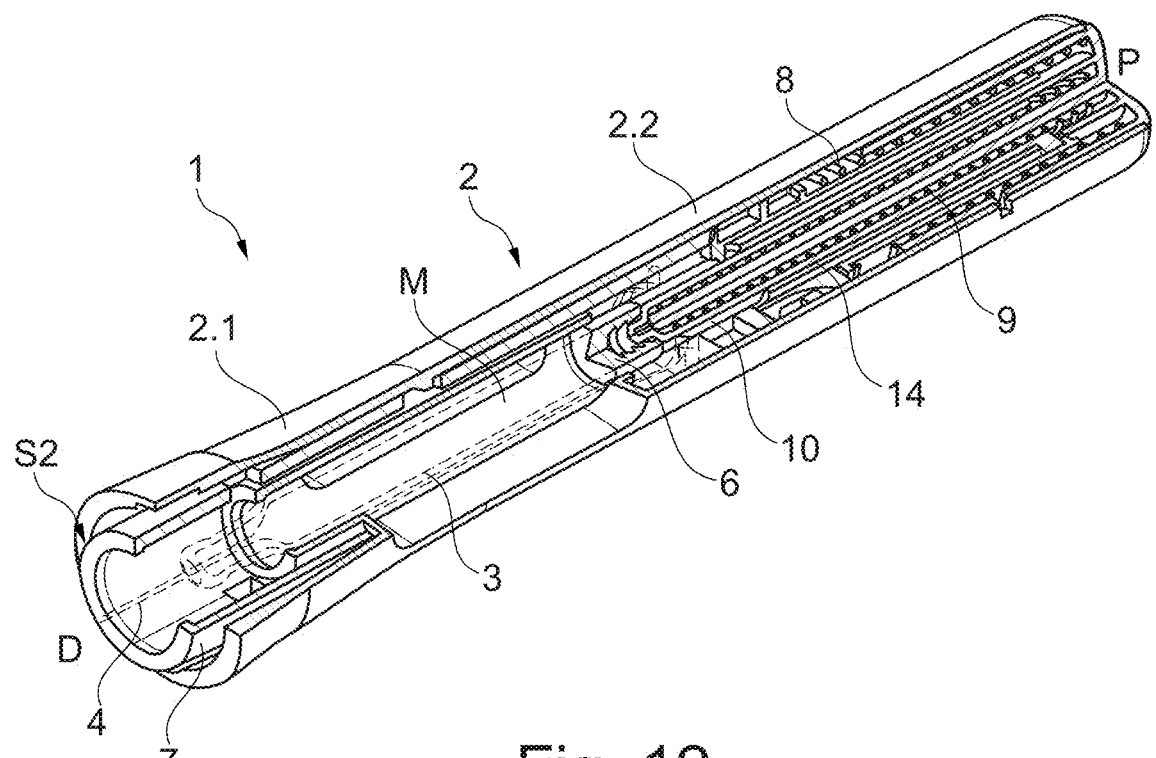
FIG. 12 is a perspective longitudinal section of the auto-injector with the needle shroud in a proximal position.

FIG. 12 is a perspective longitudinal section of the auto-injector 1 with the needle shroud 7 being fully moved in the proximal direction P into a proximal position S2 such that the needle 4 has reached the insertion depth in the injection site. Once the needle shroud 7 is fully depressed, the plunger 10 releases as shown in FIG. 7D and medicament delivery begins. The drive spring 9 begins to expand, pushing the plunger 10 in the distal direction D to inject the medicament M. The feedback mechanism 13 is in the state as illustrated in FIG. 8C. The shroud lock mechanism 15 is in the state as illustrated in FIG. 9B.

Figure 13:
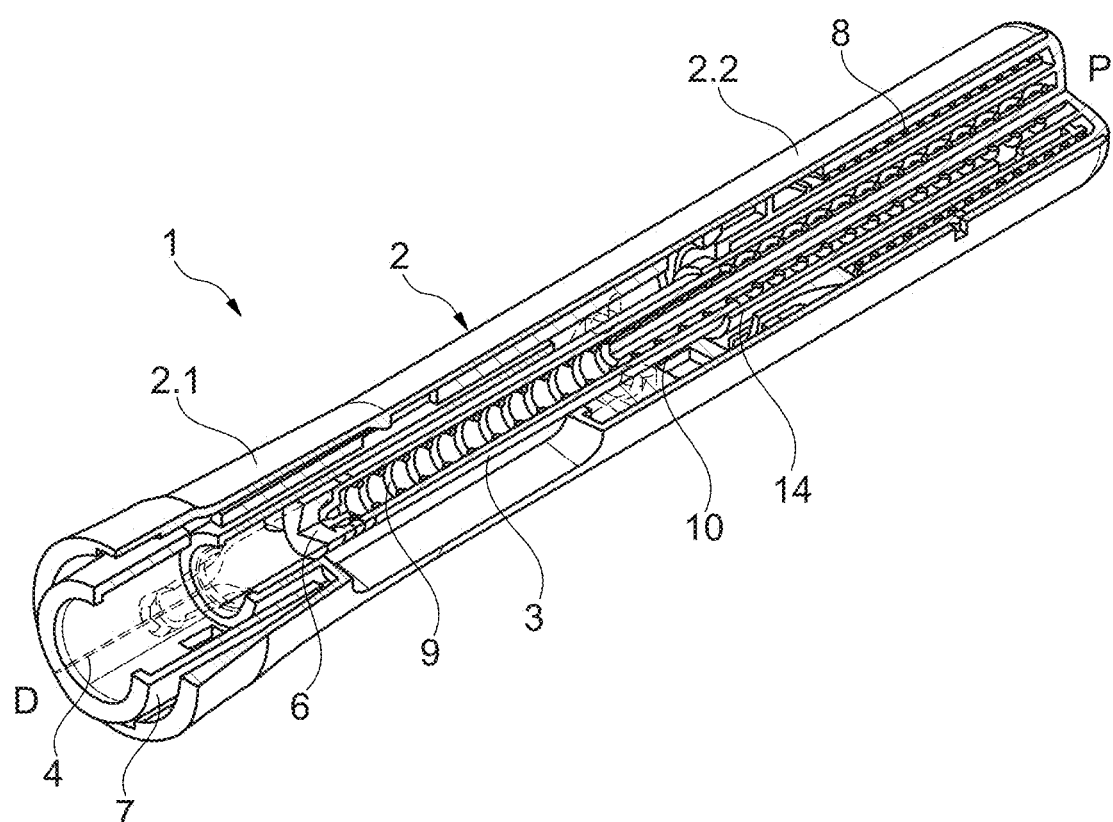
FIG. 13 is a perspective longitudinal section of the auto-injector during delivery of the medicament after release of the feedback mechanism.

FIG. 13 is a perspective longitudinal section of the auto-injector 1 during delivery of the medicament M after release of the feedback mechanism 13. As the delivery of the medicament M progresses with the plunger 10 moving down the syringe 3 barrel, the feedback mechanism 13 activates. Up to this point, the collar 14 was resting on the needle shroud 7, the needle shroud 7 preventing the collar 14 from moving further in the distal direction D. Prior to the end of the dose, the plunger 10 clears the inside of the collar 14, leaving the two first snap-fit joints 14.3 free to deflect inward. Under the force of the control spring 8, the collar 14 moves in the distal direction D, forcing its way in between the proximal arms 7.1 on the needle shroud 7. The two first snap fit joints 14.3 are deflected inward within the needle shroud 7. The feedback mechanism 13 arrives in the state as illustrated in FIG. 8D. The shroud lock mechanism 15 is in the state as illustrated in FIG. 9B.

Figure 14:
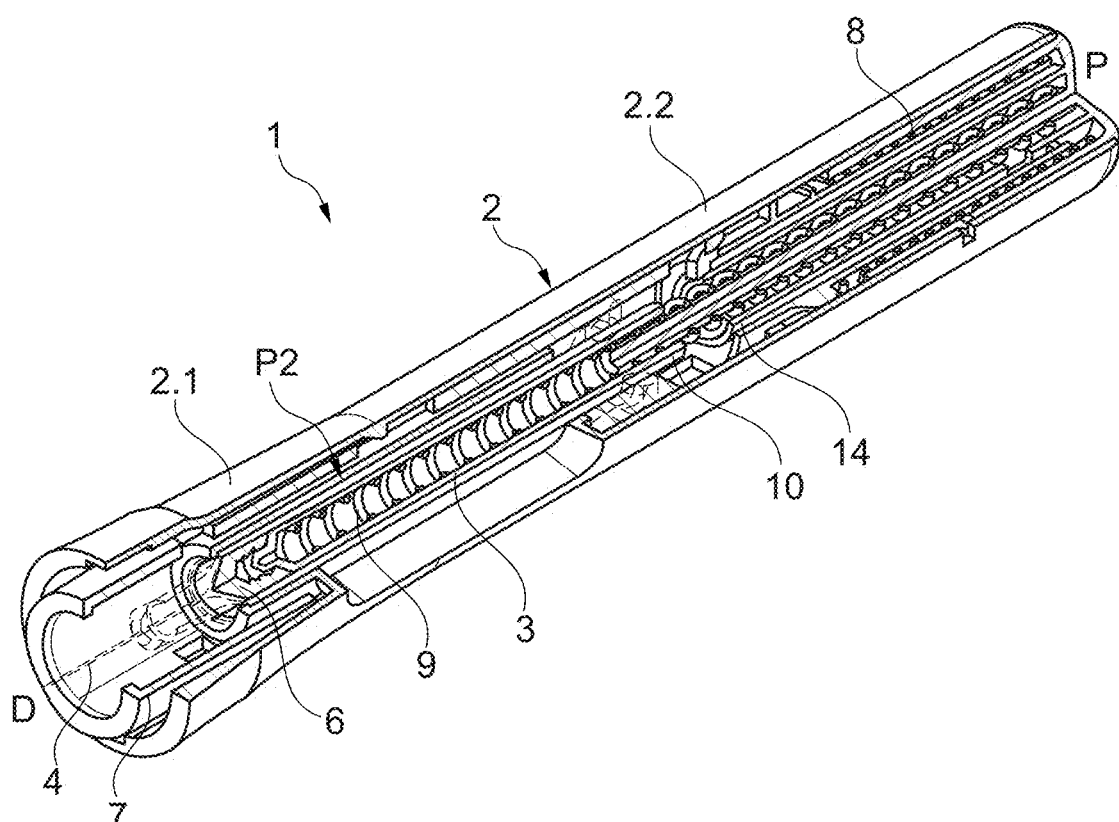
FIG. 14 is a perspective longitudinal section of the auto-injector at the end of dose prior to generation of the audible feedback.

FIG. 14 is a perspective longitudinal section of the auto-injector 1 at the end of dose prior to generation of the audible feedback. The plunger 10 has fully advanced the stopper 6 within the syringe 3 barrel and arrived at a distal position P2. Pursuing its course, the collar 14 brings the two first snap-fit joints 14.3 down to the opening 7.2 in the needle shroud 7, where the first snap-fit joints 14.3 straighten back to their initial shape. The feedback mechanism 13 arrives in the state as illustrated in FIG. 8E.

Figure 15:
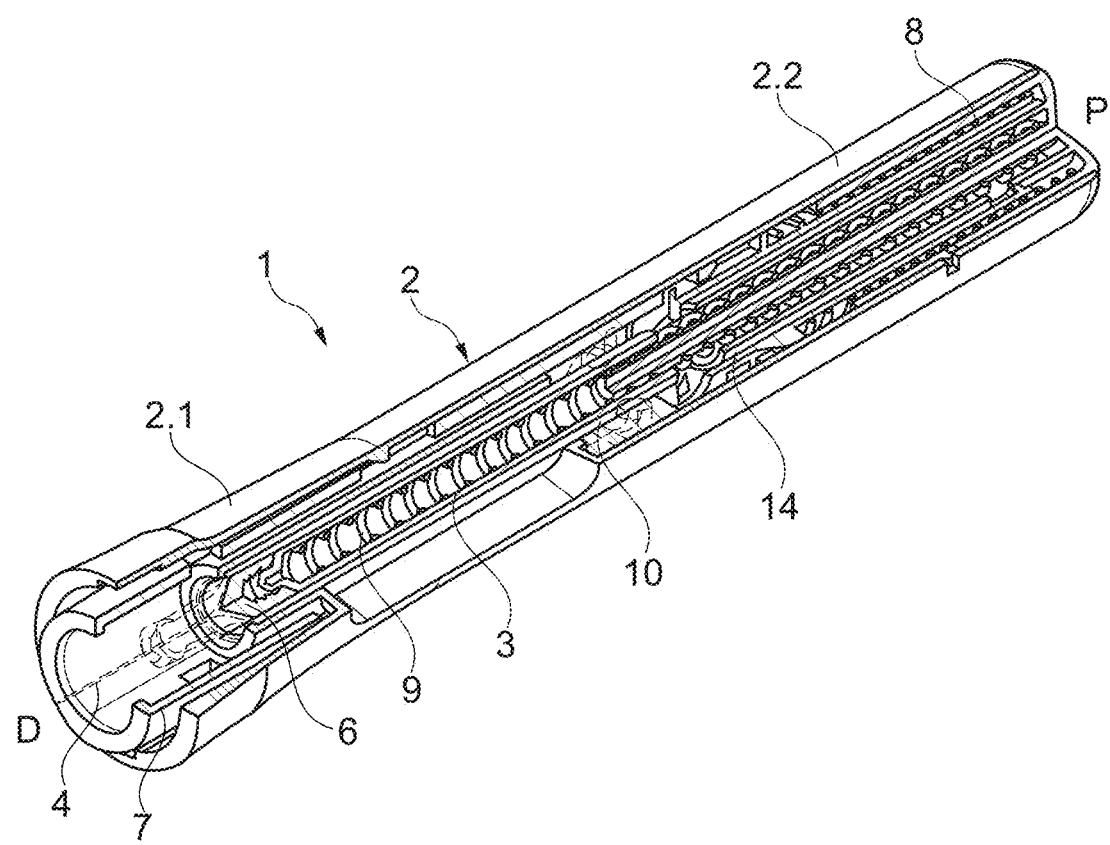
FIG. 15 is a perspective longitudinal section of the auto-injector at the end of dose after generation of the audible feedback.

FIG. 15 is a perspective longitudinal section of the auto-injector 1 at the end of dose after generation of the audible feedback. The injection is complete and an audible and/or tactile feedback is emitted through the collar 14 hitting the needle shroud 7 as the feedback mechanism 13 operates. With reduced friction, the collar 14 is propelled by the control spring 8 and the two third collar ribs 14.6 hit the needle shroud 7, creating the noise indicating that the dose is complete. The feedback mechanism 13 arrives in the state as illustrated in FIG. 8F. The shroud lock mechanism 15 is in the state as illustrated in FIG. 9C.

Figure 16:
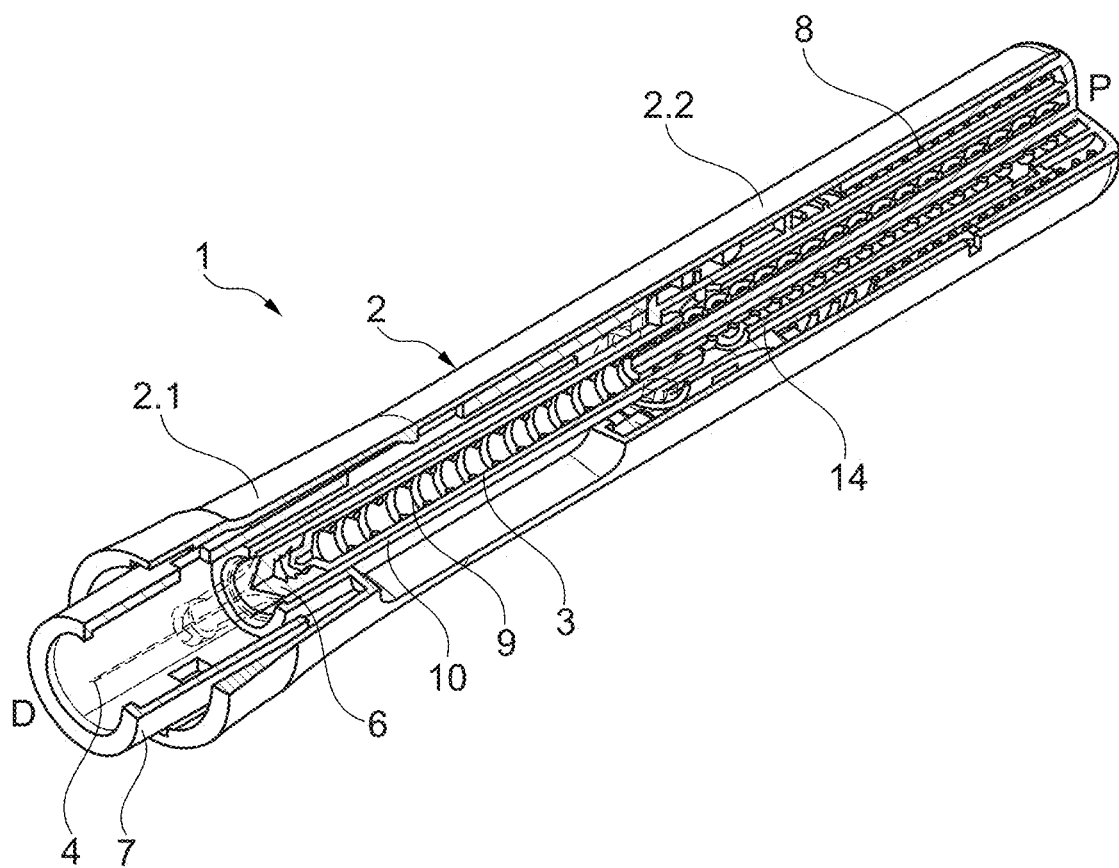
FIG. 16 is a perspective longitudinal section of the auto-injector with the needle shroud extended from the case.

FIG. 16 is a perspective longitudinal section of the auto-injector 1 post-use with the needle shroud 7 extended from the case 2. As the auto-injector 1 is moved away from the injection site, the needle shroud 7 and the collar 14, which are axially coupled as shown in FIG. 8F, advance, driven by the control spring 8. The needle shroud 7 returns to its pre-use position. However, the position of the collar 14 has evolved since the pre-use state. The two second snap-fit joints 14.7, which were so far travelling within the opening 2.8 in the rear case 2.2, move further in the distal direction D and take position just beneath the distal arms 2.9 of the rear case 2.2. This suppresses the axial degree of freedom of the collar 14 and the needle shroud 7, which are both still axially coupled. The collar 14 is locked and prevents any further axial motion of the needle shroud 7, rendering the auto-injector 1 needle safe in its post-use state. The shroud lock mechanism 15 is in the state as illustrated in FIG. 9D.

The case 2 may comprise a viewing window (not illustrated) allowing the user to examine the medicament M for clarity, observe the advancing plunger 10 for allowing to estimate the progress of the medicament delivery, and helping the user differentiate between a used and an un-used auto-injector 1.

In an exemplary embodiment, a tamper strip may be arranged between the cap 11 and the front case 2.1 when the control subassembly 1.1 is assembled.

The auto-injector 1 may be placed against the injection site multiple times without any adverse effect to the mechanism. The force to depress the needle shroud 7 may be less than 6 N.

The syringe 3 used in the auto-injector 1 may for example be a 1 ml syringe 3.

The auto-injector 1 is always needle safe as the needle can be retracted before the delivery of the medicament M is complete.

As only the plunger 10 and the rear case 2.2 are subjected to the relatively high force of the drive spring 9, the other components of the auto-injector 1 are not affected, so reliability and shelf life are increased.

The auto-injector 1 is suited to be used as a platform as the drive spring 9 can be swapped to deliver different viscosity drugs without affecting the insertion or retraction functions. This is particularly advantageous for high viscosity fluids.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')$_2$ fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 auto-injector
1.1 control subassembly
1.2 drive subassembly
2 case
2.1 front case
2.2 rear case
2.3 inner rib
2.4 opening
2.5 angled surface
2.6 proximal end
2.8 opening
2.9 distal arm
3 syringe
4 injection needle
5 protective needle sheath
6 stopper
7 needle shroud
7.1 proximal arm
7.2 opening
8 control spring
9 drive spring
10 plunger
10.1 rib
11 cap
12 plunger release mechanism
13 feedback mechanism
14 collar
14.1 first collar rib
14.2 second collar rib
14.3 first snap-fit joint
14.4 inner protrusion
14.5 angled surface
14.6 third collar rib
14.7 second snap-fit joint
14.8 angled surface
14.9 proximal surface
15 shroud lock mechanism
A advanced position
D distal direction
M medicament
P proximal direction
P1 proximal position
P2 distal position
R1 rotational direction
R2 rotational direction
S1 distal position
S2 proximal position

The invention claimed is:

1. An autoinjector comprising:
a case adapted to receive at least a portion of a medicament container;
a plunger movable relative to the case along a longitudinal axis of the autoinjector between an initial position and a drug delivery position for delivering a medicament from the medicament container;
an inner sleeve configured to engage a proximal end of the plunger when the plunger is in the initial position, the inner sleeve comprising a tubular body and a flexible arm movable relative to the tubular body, the flexible arm comprising a first end coupled to the tubular body and a second end spaced from the tubular body, wherein the flexible arm is movable between an inwardly deflected position and a relaxed position; and
an outer sleeve comprising a sleeve body having a first end, a second end, and an interior surface defining a cylindrical cavity, the sleeve body comprising an opening radially extending through the sleeve body and longitudinally extending between the first end and the second end, wherein the opening is sized to receive a portion of the flexible arm,
wherein the autoinjector is configured such that after the plunger moves into the drug delivery position, the inner sleeve moves axially relative to the outer sleeve and into the cylindrical cavity of the outer sleeve, allowing the flexible arm to engage the interior surface of the outer sleeve and deflecting the flexible arm inwardly, and
wherein the autoinjector is configured such that an audible signal or a tactile signal is generated from an impact event between the inner sleeve and the outer sleeve to indicate completion of dispensing of the medicament.

2. The autoinjector of claim 1, wherein the flexible arm comprises a projection extending radially outward relative to the longitudinal axis.

3. The autoinjector of claim 2, wherein the opening in the outer sleeve is sized to receive the projection of the flexible arm.

4. The autoinjector of claim 2, wherein the projection is configured to engage the interior surface of the outer sleeve.

5. The autoinjector of claim 2, wherein the autoinjector is configured such that when the projection moves into the opening in the outer sleeve, the flexible arm moves into the relaxed position.

6. The autoinjector of claim 1, comprising the medicament container containing the medicament, the medicament comprising a glucagon-like peptide-1 (GLP-1) or an analogue or derivative thereof.

7. The autoinjector of claim 1, comprising a control spring coupled to the inner sleeve, and configured to transition from an energized state to an expanded state after the plunger moves into the drug delivery position.

8. The autoinjector of claim 7, wherein the inner sleeve is configured to move axially relative to the outer sleeve under a biasing force of the control spring when the control spring transitions into the expanded state.

9. The autoinjector of claim 7, comprising a drive spring having (i) a distal end in direct engagement with the plunger for biasing the plunger in a distal direction and (ii) a proximal end held in a fixed axial location as the plunger moves in the distal direction.

10. The autoinjector of claim 1, wherein the autoinjector is configured such that when the flexible arm moves into the opening in the outer sleeve, the flexible arm moves into the relaxed position and the inner sleeve is configured to impact the outer sleeve to generate the audible signal or the tactile signal to indicate completion of dispensing of the medicament.

11. An autoinjector comprising:
a plunger movable along a longitudinal axis of the autoinjector between an initial position and a drug delivery position for delivering a medicament from a medicament container;
an inner sleeve configured to surround a proximal end of the plunger when the plunger is in the initial position, the inner sleeve comprising a tubular body and a flexible arm movable relative to the tubular body, the flexible arm comprising a first end coupled to the tubular body and a second end spaced from the tubular body, wherein the flexible arm is movable between an inwardly deflected position and a relaxed position; and
an outer sleeve comprising a sleeve body having a first end, a second end, and an interior surface defining a cylindrical cavity, the sleeve body comprising an opening radially extending through the sleeve body and longitudinally extending between the first end and the second end, wherein the opening is sized to receive a portion of the flexible arm,
wherein the autoinjector is configured such that after the plunger moves into the drug delivery position, the inner sleeve moves axially relative to the outer sleeve and into the cylindrical cavity of the outer sleeve, allowing the flexible arm to engage the interior surface of the outer sleeve and deflecting the flexible arm inwardly, and
wherein the autoinjector is configured such that an audible signal or a tactile signal is generated from an impact event between the inner sleeve and the outer sleeve to indicate completion of dispensing of the medicament.

12. The autoinjector of claim 11, wherein the flexible arm comprises a projection extending radially outward relative to the longitudinal axis.

13. The autoinjector of claim 12, wherein the opening in the outer sleeve is sized to receive the projection of the flexible arm.

14. The autoinjector of claim 12, wherein the projection is configured to engage the interior surface of the outer sleeve.

15. The autoinjector of claim 12, wherein the autoinjector is configured such that when the projection moves into the opening in the outer sleeve, the flexible arm moves into the relaxed position.

16. The autoinjector of claim 11, comprising a control spring coupled to the inner sleeve, and configured to transition from an energized state to an expanded state after the plunger moves into the drug delivery position.

17. The autoinjector of claim 16, wherein the inner sleeve is configured to move axially relative to the outer sleeve under a biasing force of the control spring when the control spring transitions into the expanded state.

18. The autoinjector of claim 16, comprising a drive spring having (i) a distal end in direct engagement with the plunger for biasing the plunger in a distal direction and (ii) a proximal end held in a fixed axial location as the plunger moves in the distal direction.

19. The autoinjector of claim 11, wherein the autoinjector is configured such that when the flexible arm moves into the opening in the outer sleeve, the flexible arm moves into the relaxed position and the inner sleeve is configured to impact the outer sleeve to generate the audible signal or the tactile signal to indicate completion of dispensing of the medicament.

20. A drug delivery device comprising:
a plunger movable along a longitudinal axis of the drug delivery device between an initial position and a drug delivery position for delivering a medicament from a medicament container;
an inner sleeve arranged around a proximal end of the plunger when the plunger is in the initial position, the inner sleeve comprising an inner sleeve body and a flexible arm extending from the inner sleeve body, wherein the flexible arm is movable relative to the inner sleeve body between an inwardly deflected position and a relaxed position; and
an outer sleeve comprising an outer sleeve body having an interior surface defining an interior space, the outer sleeve body comprising an opening radially extending through the outer sleeve body, wherein the opening is sized to receive a portion of the flexible arm,
wherein the drug delivery device is configured such that after the plunger moves into the drug delivery position, the inner sleeve moves axially relative to the outer sleeve and into the interior space of the outer sleeve, allowing the flexible arm to engage the interior surface of the outer sleeve and deflecting the flexible arm inwardly, and
wherein the drug delivery device is configured such that an audible signal or a tactile signal is generated from an impact event between the inner sleeve and the outer sleeve to indicate completion of dispensing of the medicament.

21. The drug delivery device of claim 20, wherein the drug delivery device is configured such that when the flexible arm moves into the opening in the outer sleeve, the flexible arm moves into the relaxed position and the inner sleeve is configured to impact the outer sleeve to generate the audible signal or the tactile signal to indicate completion of dispensing of the medicament.

22. The drug delivery device of claim 20, wherein the flexible arm comprises a first end coupled to the inner sleeve body and a second end spaced from the inner sleeve body.

23. The drug delivery device of claim 22, wherein the flexible arm comprises a projection extending radially outward relative to the longitudinal axis.

24. The drug delivery device of claim 23, wherein the projection is configured to engage the interior surface of the outer sleeve.

25. The drug delivery device of claim 23, wherein the drug delivery device is configured such that when the projection moves into the opening in the outer sleeve, the flexible arm moves into the relaxed position.

26. The drug delivery device of claim 23, comprising a spring coupled to the inner sleeve, and configured to transition from an energized state to an expanded state after the plunger moves into the drug delivery position.

27. The drug delivery device of claim 26, wherein the inner sleeve is configured to move axially relative to the outer sleeve under a biasing force of the spring when the spring transitions into the expanded state.

28. The drug delivery device of claim 21, wherein the outer sleeve body comprises a first end and a second end, and wherein the opening longitudinally extends between the first end and the second end of the outer sleeve body.

29. The drug delivery device of claim 21, comprising the medicament container configured to hold the medicament, and a needle coupled to a distal end of the medicament container.

30. The drug delivery device of claim 21, comprising the medicament container containing the medicament, the medicament comprising a glucagon-like peptide-1 (GLP-1) or an analogue or derivative thereof.

* * * * *